US012614439B2

(12) United States Patent　　(10) Patent No.:　US 12,614,439 B2
Mieno et al.　　(45) Date of Patent:　Apr. 28, 2026

(54) INFORMATION PROCESSING SYSTEM, INFORMATION PROCESSING APPARATUS, INFORMATION PROCESSING METHOD, AND NON-TRANSITORY COMPUTER-READABLE MEDIUM

(71) Applicant: PARAMOUNT BED CO., LTD., Tokyo (JP)

(72) Inventors: Tsutomu Mieno, Kanagawa (JP); Mutsumi Onodera, Kanagawa (JP); Hiroshi Saito, Kanagawa (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 74 days.

(21) Appl. No.: 18/692,878

(22) PCT Filed: Oct. 4, 2022

(86) PCT No.: PCT/JP2022/037109
§ 371 (c)(1),
(2) Date: Mar. 18, 2024

(87) PCT Pub. No.: WO2023/074276
PCT Pub. Date: May 4, 2023

(65) Prior Publication Data
US 2024/0428670 A1　Dec. 26, 2024

(30) Foreign Application Priority Data
Oct. 26, 2021　(JP) ................................. 2021-174624

(51) Int. Cl.
*G08B 23/00*　(2006.01)
*G08B 21/02*　(2006.01)
*G16H 40/20*　(2018.01)

(52) U.S. Cl.
CPC ............. *G08B 21/02* (2013.01); *G16H 40/20* (2018.01)

(58) Field of Classification Search
CPC ........ G08B 21/02; G08B 21/22; G08B 25/00; G08B 25/04; G16H 40/20; G06Q 50/22
(Continued)

(56) References Cited

U.S. PATENT DOCUMENTS 8,344,893 B1 * 1/2013 Drammeh ............ G08B 21/245
340/573.1
10,289,917 B1 * 5/2019 Fu .................... G08B 13/19602
(Continued)

FOREIGN PATENT DOCUMENTS

JP　2000-261566 A　9/2000
JP　2008-282219 A　11/2008
(Continued)

OTHER PUBLICATIONS

Japanese Office Action for JP Application No. 2021-174624 mailed on Apr. 2, 2024 with English Translation.
(Continued)

*Primary Examiner* — Tai T Nguyen
(74) *Attorney, Agent, or Firm* — Wenderoth, Lind & Ponack, L.L.P.

(57) ABSTRACT

An information processing system includes a sensor that detects entry of a person into a room, and determines whether the person who enters the room is a care recipient as a user of the room or a caregiver who provides care for the user. The information processing system specifies a person who enters the room, and stores an entry detection result by the sensor, a determination result, and a specification result. The information processing system outputs first notification information indicating the entry detection result, second notification information indicating the determination
(Continued)

INFORMATION PROCESSING SYSTEM

SENSOR — 1a

DETERMINATION UNIT — 1b

SPECIFICATION UNIT — 1c

STORAGE UNIT — 1d

OUTPUT UNIT — 1e result, and third notification information indicating the specification result to a notification destination.

20 Claims, 10 Drawing Sheets

(58) Field of Classification Search
USPC ........................................................ 340/573.1
See application file for complete search history.

(56) References Cited

U.S. PATENT DOCUMENTS

| | | | | |
|---|---|---|---|---|
| 11,581,099 | B1 * | 2/2023 | Rufo ...................... | G16H 20/13 |
| 2009/0091458 | A1 * | 4/2009 | Deutsch ................. | G16H 40/20 |
| | | | | 705/2 |
| 2017/0358193 | A1 * | 12/2017 | Ribble .............. | G08B 21/0461 |
| 2019/0156496 | A1 * | 5/2019 | Leduc .................... | G06V 10/62 |
| 2020/0302775 | A1 * | 9/2020 | Liu ..................... | G06K 7/10366 |
| 2020/0365002 | A1 * | 11/2020 | Modiano .............. | A61B 5/7405 |
| 2021/0166551 | A1 * | 6/2021 | Cross ..................... | G16H 15/00 |

FOREIGN PATENT DOCUMENTS

| | | | |
|---|---|---|---|
| JP | 2014-186402 | A | 10/2014 |
| JP | 2015-056031 | A | 3/2015 |
| JP | 2016-057979 | A | 4/2016 |
| JP | 2017-027574 | A | 2/2017 |
| JP | 2017-117423 | A | 6/2017 |
| JP | 2020-112902 | A | 7/2020 |
| JP | 2021-012744 | A | 2/2021 |
| JP | 2021-111268 | A | 8/2021 |
| JP | 2022-092102 | A | 6/2022 |
| WO | 2016/194402 | A1 | 12/2016 |
| WO | 2017/061371 | A1 | 4/2017 |
| WO | 2020/066761 | A1 | 4/2020 |
| WO | 2021/024584 | A1 | 2/2021 |

OTHER PUBLICATIONS

JP Office Communication for JP Application No. 2021-174624, mailed on Jul. 2, 2024 with English Translation.
International Search Report for PCT Application No. PCT/JP2022/037109, mailed on Dec. 13, 2022.

* cited by examiner

INFORMATION PROCESSING SYSTEM, INFORMATION PROCESSING APPARATUS, INFORMATION PROCESSING METHOD, AND NON-TRANSITORY COMPUTER-READABLE MEDIUM

This application is a National Stage Entry of PCT/JP2022/037109 filed on Oct. 4, 2022, which claims priority from JP Patent Application 2021-174624 filed on Oct. 26, 2021, the contents of all of which are incorporated herein by reference, in their entirety.

TECHNICAL FIELD

The present disclosure relates to an information processing system, an information processing apparatus, an information processing method, and a program.

BACKGROUND ART

In a caregiving site in a care facility, a residence, or the like, a caregiver watches over a care recipient (care receiver) in order to understand his/her situation and provide assistance.

In connection with an assistance of excretion, Patent Literature 1 describes a technique in which a controller having a communication unit and a human detecting sensor for a toilet are installed in a residence of a person to be monitored, and a usage status of the toilet of the person to be monitored is monitored by a monitoring server by using the human detecting sensor for a toilet. The controller notifies a monitoring server of state information (entry information or exit information) including date and time information at this time point and identification information such as a target ID or a name of the person to be monitored when entry to the toilet and exit from the toilet by the person to be monitored are detected. Then, the monitoring server accumulates the entry information and the exit information being notified from the controller, and periodically determines whether an emergency state to be warned occurs, based on the accumulated entry information and exit information. Then, when occurrence of the emergency state is detected, the monitoring server transmits warning information to a predetermined portable terminal apparatus.

CITATION LIST

Patent Literature

[Patent Literature 1] Japanese Unexamined Patent Application Publication No. 2016-057979

SUMMARY OF INVENTION

As described above, the caregiver watches a situation of the care receiver and provides assistance, but there are the following problems in performing those works.

Firstly, a single caregiver is in charge of a plurality of care receivers, and although a priority varies depending on a degree of nursing care, the caregiver watches over the care receiver in order to understand the situation and provide assistance. However, there is a problem that a caregiver has a large burden on watching over a care receiver, due to a fact that it takes a long period of time for the caregiver to watch over the care receiver, and the caregiver cannot handle other works, for example.

Secondly, as a method of reducing watching, there is a method of installing a watching camera and watching over the care receiver. However, it is not possible to use a video photographed by the watching camera as it is for watching because of a privacy problem and dignity of the care receiver being impaired. Therefore, a method of notifying a caregiver by displaying a care receiver as a silhouette or by estimating an action by skeleton estimation or the like from a video is conceivable. However, even in these methods, in a privacy space such as a toilet, a bath, or other private rooms, there is a problem in constantly watching and it is not suitable for use. Therefore, there is a problem that the watching camera cannot be used in a place belonging to the privacy space, and that there is a place where the burden on watching cannot be reduced.

Thirdly, as a method for solving the second problem, there is a method of installing a human detecting sensor in a toilet, a bath, or the like, and a notification apparatus that notifies in a case of detecting a person by the human detecting sensor, but it cannot be understood who enters the room. Therefore, there arises a problem that a caregiver takes wasteful labor in watching, such as going to a site for confirmation once, providing assistance when assistance is necessary, and returning to another work when assistance is unnecessary. In addition, even when assistance is required, need for assistance varies depending on each care receiver and there is a person in charge that matches the care receiver, and therefore, there also arises a problem that a response is delayed when the person goes to the site once and confirms who is there.

Fourthly, in the above-described system including the human detecting sensor and the notification apparatus, although it is not necessary to notify entry to the room when a caregiver uses the room or at a time of cleaning, there is a problem that wasteful labor is required in watching, such as a wasteful notification being given and another caregiver rushing thereto.

In order to improve the above-described situation, a mechanism is desired in which an entry status of a care receiver into a room to be watched is notified, and information (individual identification information) for specifying an individual person entering the room is further notified to the caregiver. The technique described in Patent Literature 1 is based on a premise that a person in a residence uses a toilet, and the above-described problems cannot be solved.

The present disclosure has been made for solving the above-described problems and provides an information processing system, an information processing apparatus, an information processing method, and a program that are capable of notifying a caregiver of an entry status of a care receiver into a room to be watched and information for specifying an individual person entering the room.

An information processing system according to a first aspect of the present disclosure includes: a sensor configured to detect entry of a person into a room; and a determination unit configured to determine whether the person who enters the room is a care recipient as a user of the room or a caregiver who provides care for the user. The information processing system includes: a specification unit configured to specify the person: and a storage unit configured to store an entry detection result by the sensor, a determination result by the determination unit, and a specification result by the specification unit. The information processing system includes an output unit configured to output first notification information indicating the entry detection result, second notification information indicating the determination result, and third notification information indicating the specification result to a notification destination.

An information processing apparatus according to a second aspect of the present disclosure includes: a sensor configured to detect entry of a person into a room: and a determination unit configured to determine whether the person who enters the room is a care recipient as a user of the room or a caregiver who provides care for the user. The information processing apparatus includes: a specification unit configured to specify the person: and a storage unit configured to store an entry detection result by the sensor, a determination result by the determination unit, and a specification result by the specification unit. The information processing apparatus includes an output unit configured to output first notification information indicating the entry detection result, second notification information indicating the determination result, and third notification information indicating the specification result to a notification destination.

An information processing method according to a third aspect of the present disclosure includes: detecting entry of a person into a room by a sensor; determining whether the person who enters the room is a care recipient as a user of the room or a caregiver who provides care for the user: and specifying the person. The information processing method includes: storing an entry detection result by the sensor, a determination result acquired by determining the person, and a specification result acquired by specifying the person: and outputting first notification information indicating the entry detection result, second notification information indicating the determination result, and third notification information indicating the specification result to a notification destination.

A program according to a fourth aspect of the present disclosure causes a computer to execute information processing of inputting an entry detection result in which entry of a person into a room is detected by a sensor. The information processing includes processing of: determining whether the person who enters the room is a care recipient as a user of the room or a caregiver who provides care for the user: and specifying the person. The information processing includes processing of: storing an entry detection result by the sensor, a determination result acquired by determining the person, and a specification result acquired by specifying the person: and outputting first notification information indicating the entry detection result, second notification information indicating the determination result, and third notification information indicating the specification result to a notification destination.

According to the present disclosure, it is possible to provide an information processing system, an information processing apparatus, an information processing method, and a program that are capable of notifying a caregiver of an entry status of a care receiver into a room to be watched, and information for specifying an individual person entering the room.

4

Figure 2:
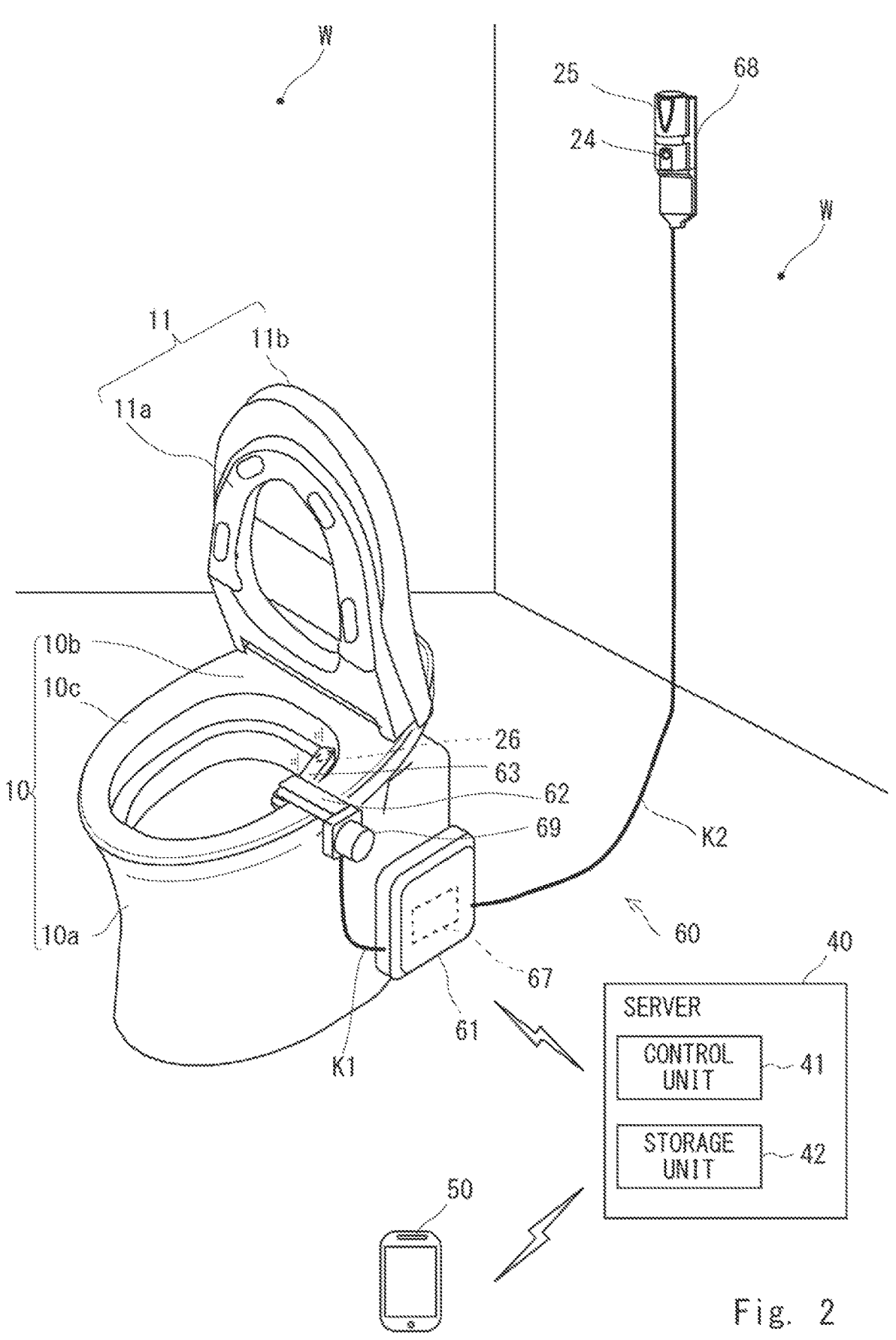
FIG. 2 is a diagram illustrating a configuration example of an information processing system according to a second example embodiment.
Figure 3:
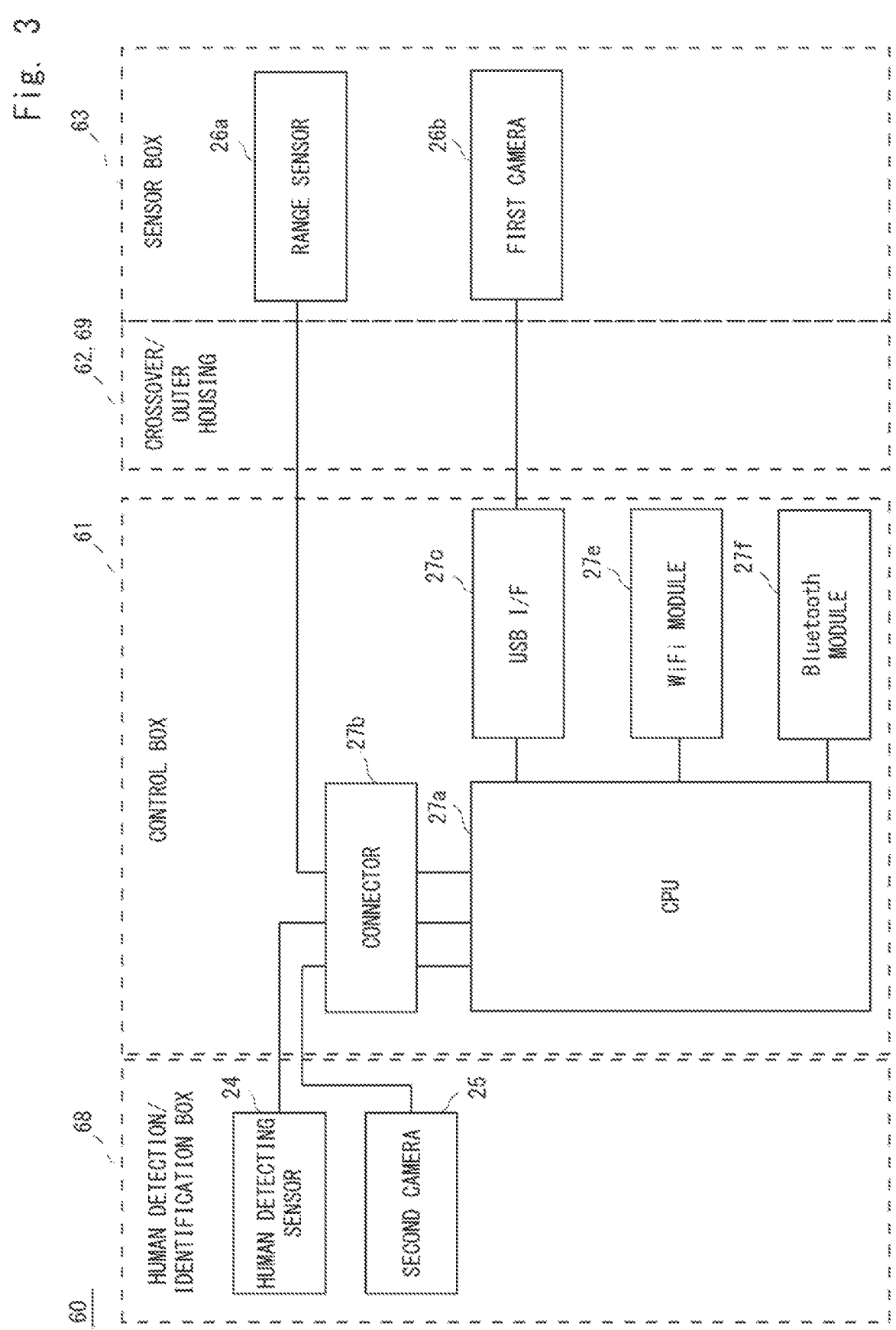
Figure 4:
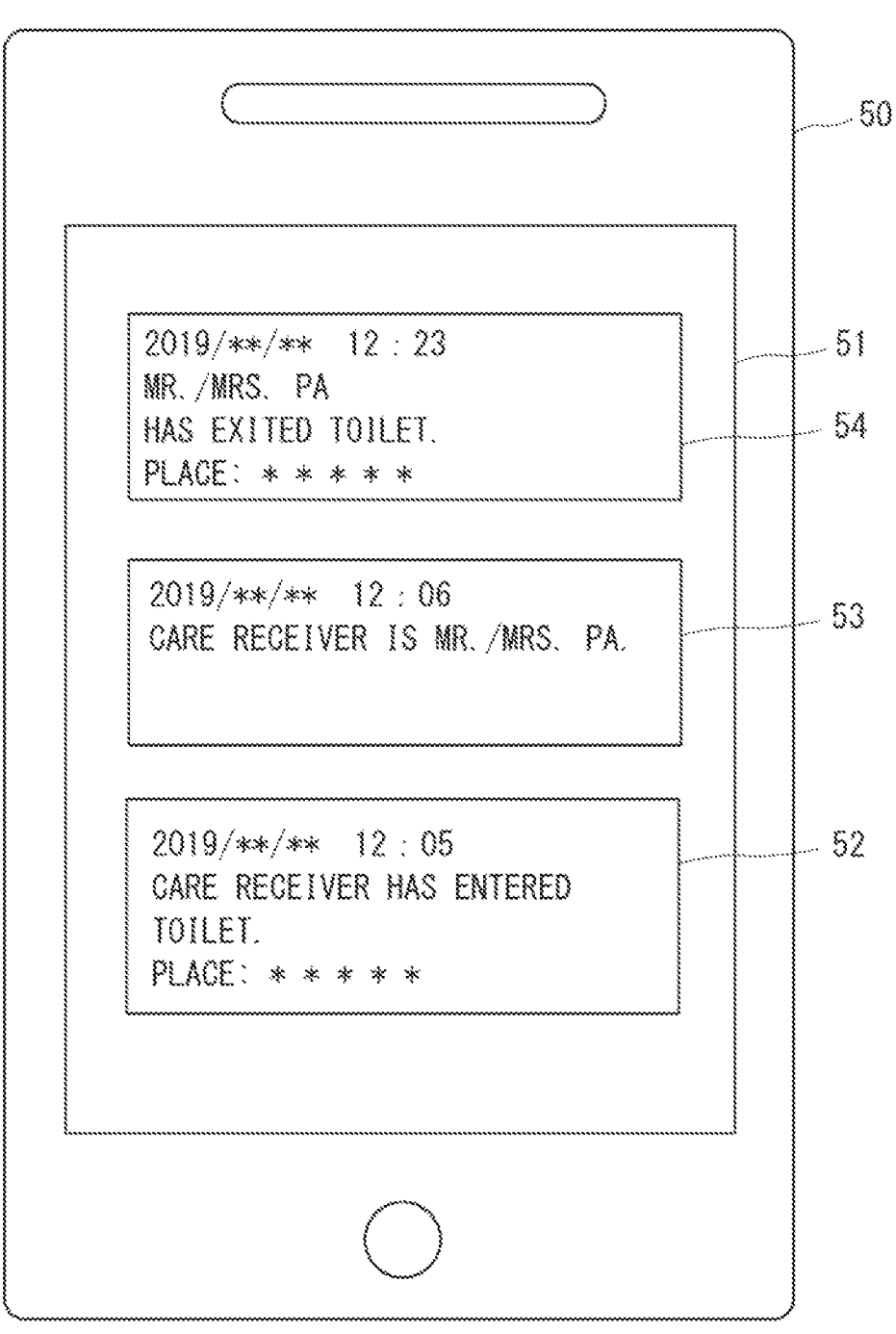
Figure 5:
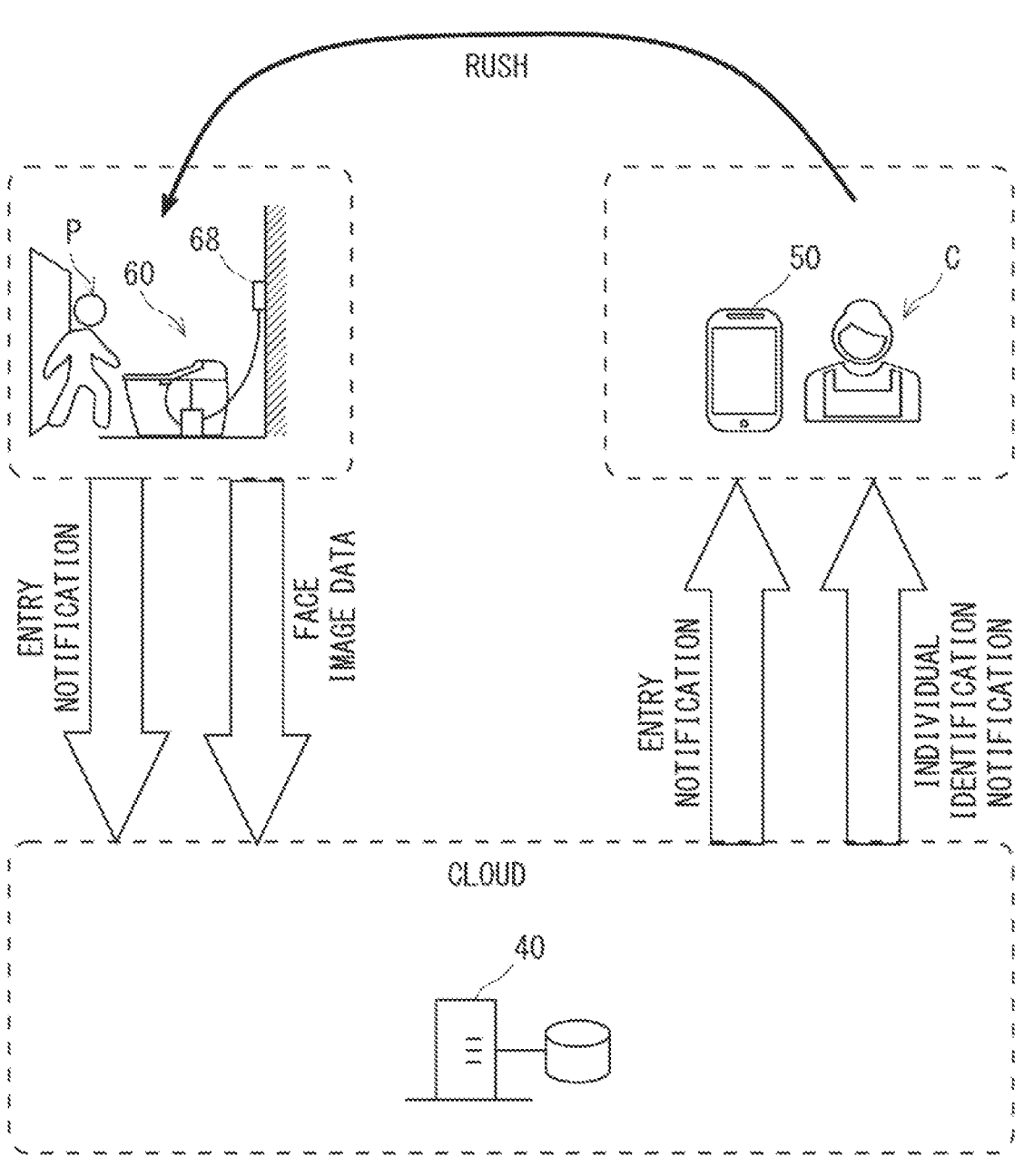
Figure 6:
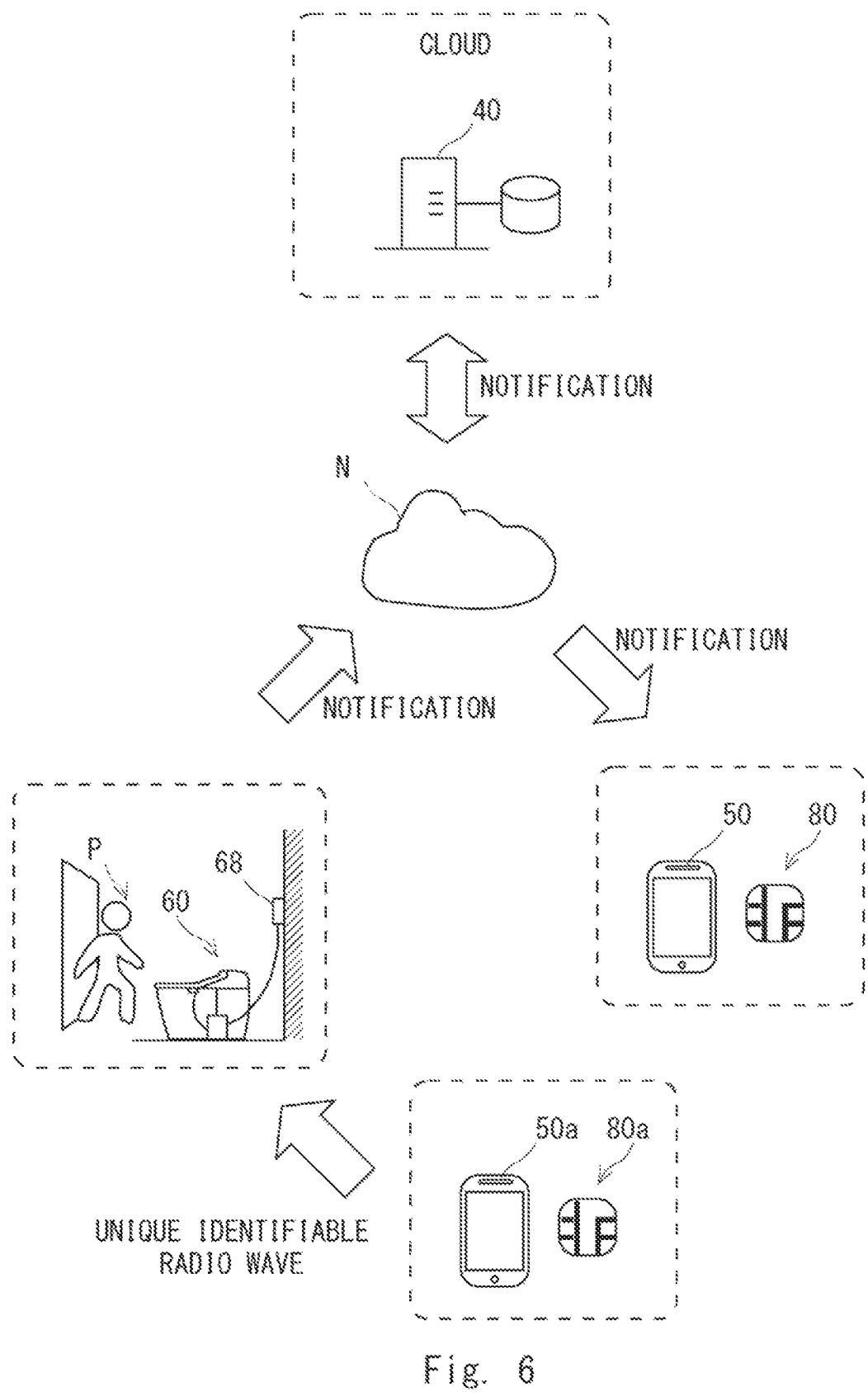
Figure 7:
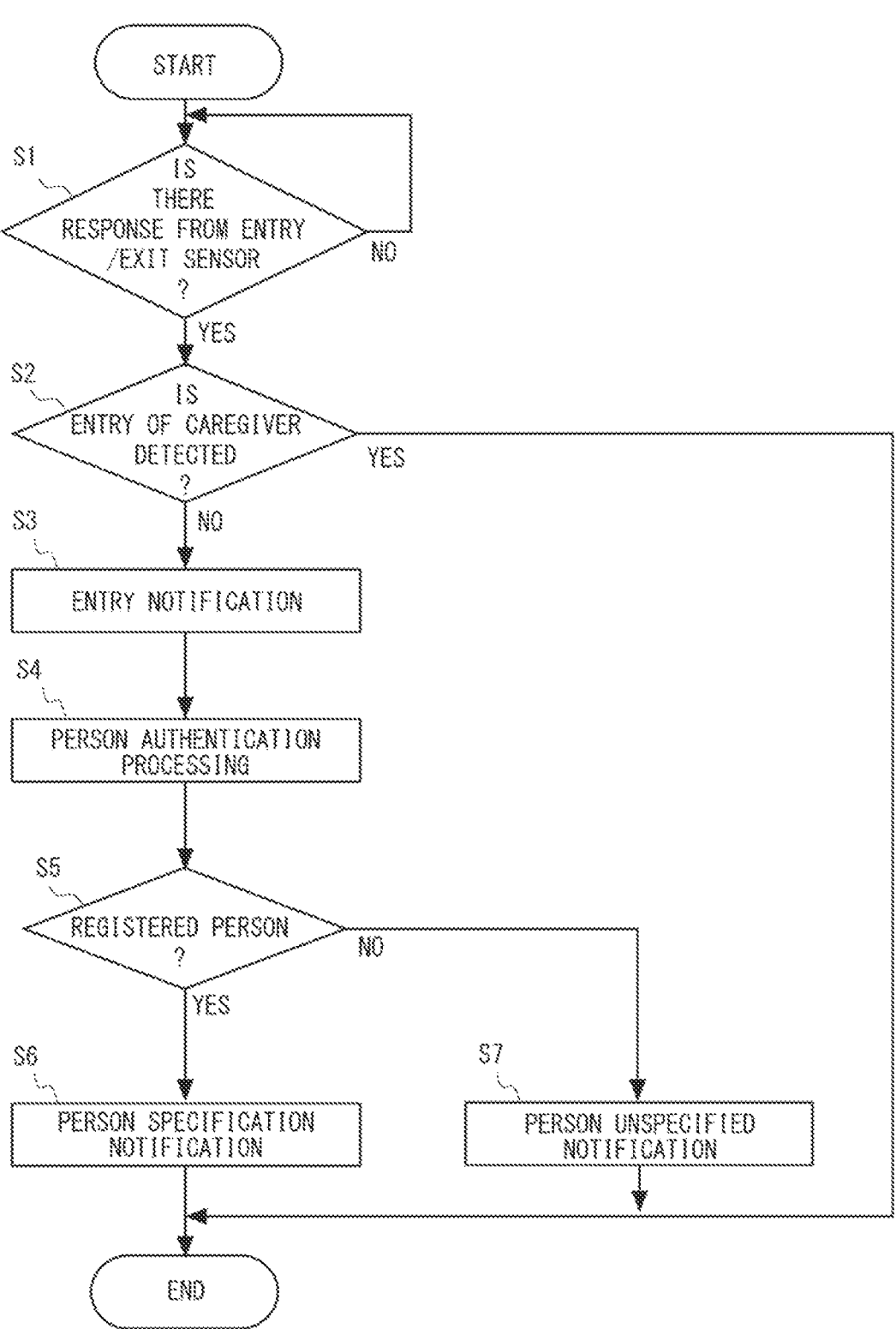
Figure 8:
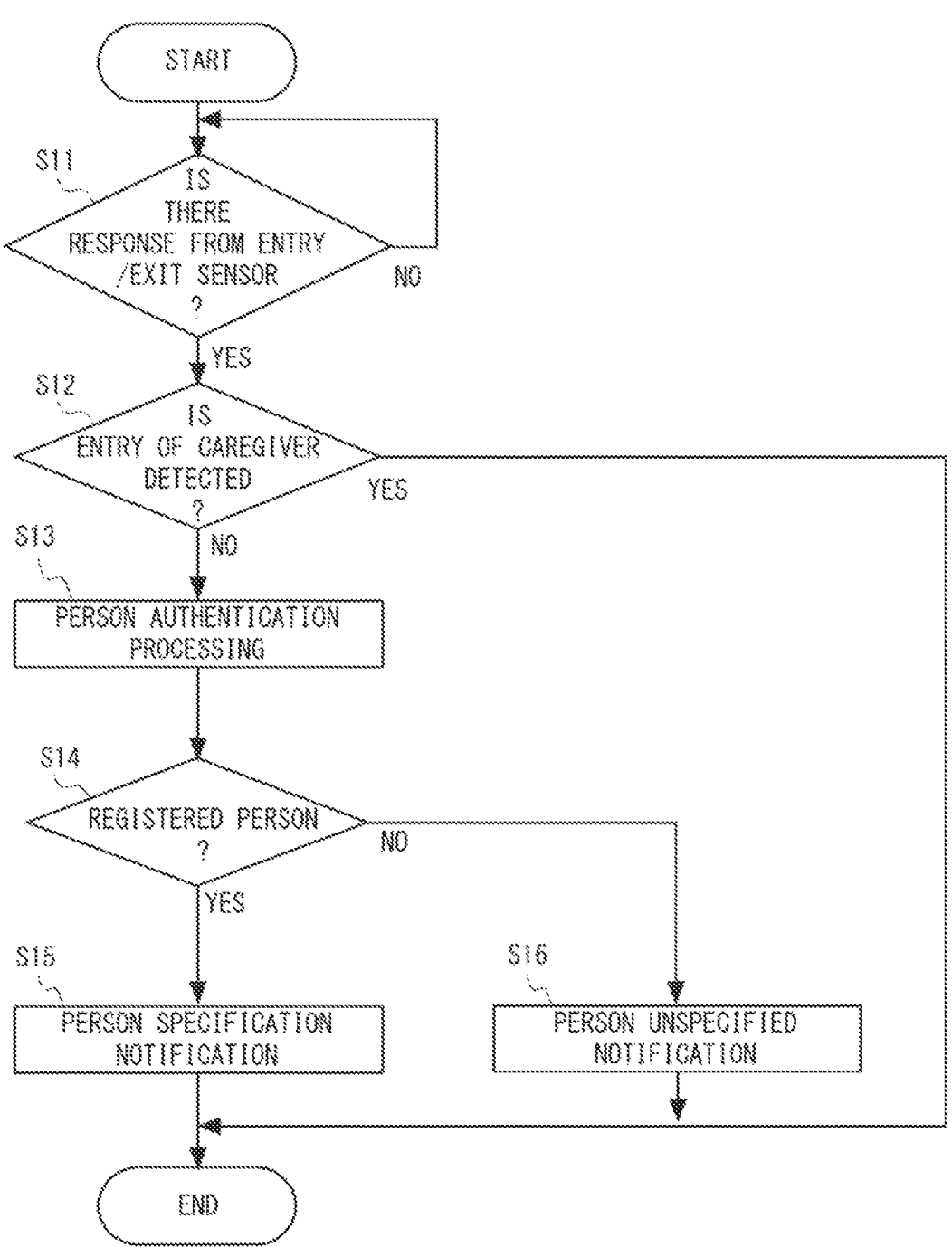
Figure 9:
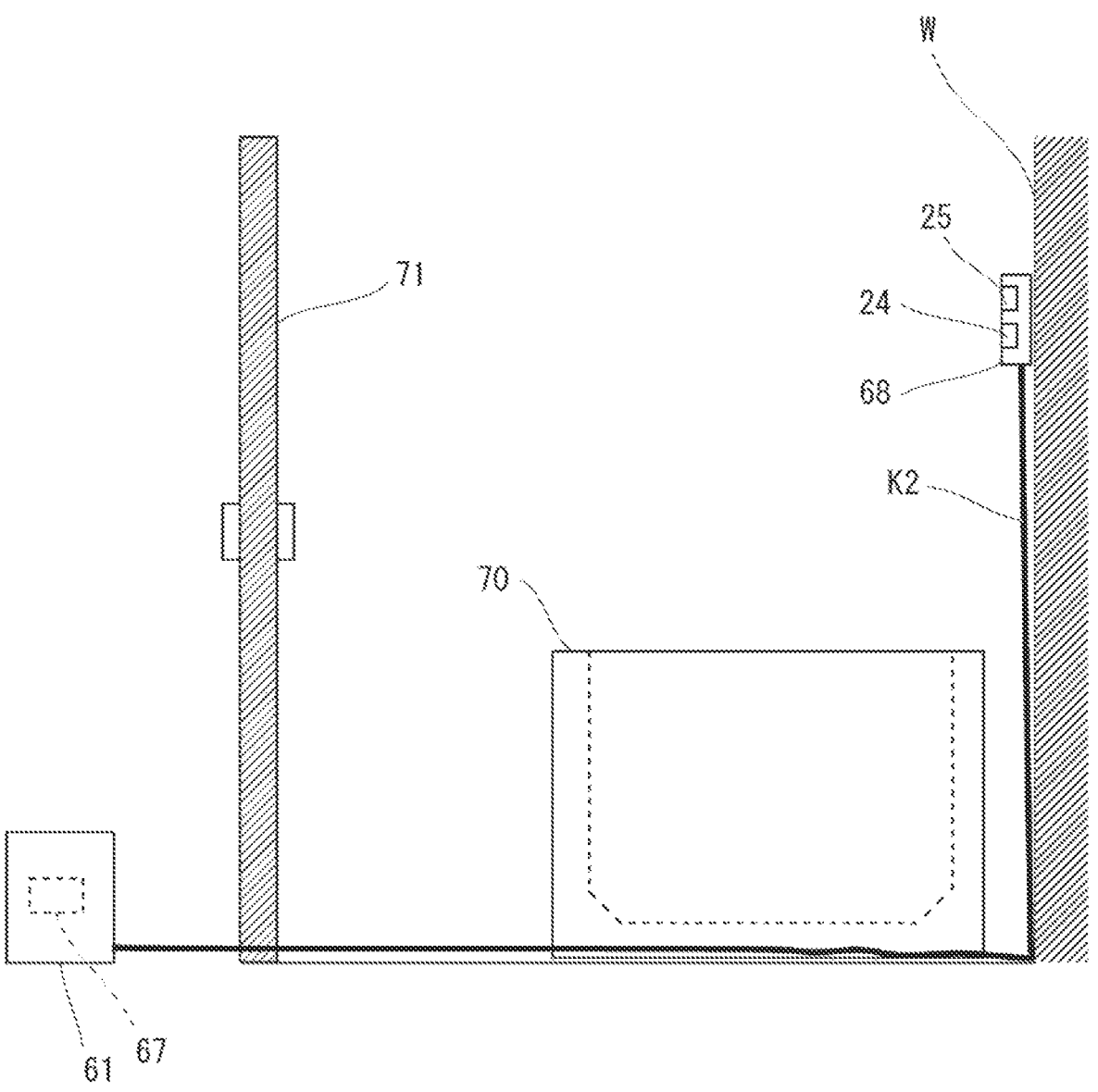
Figure 10:
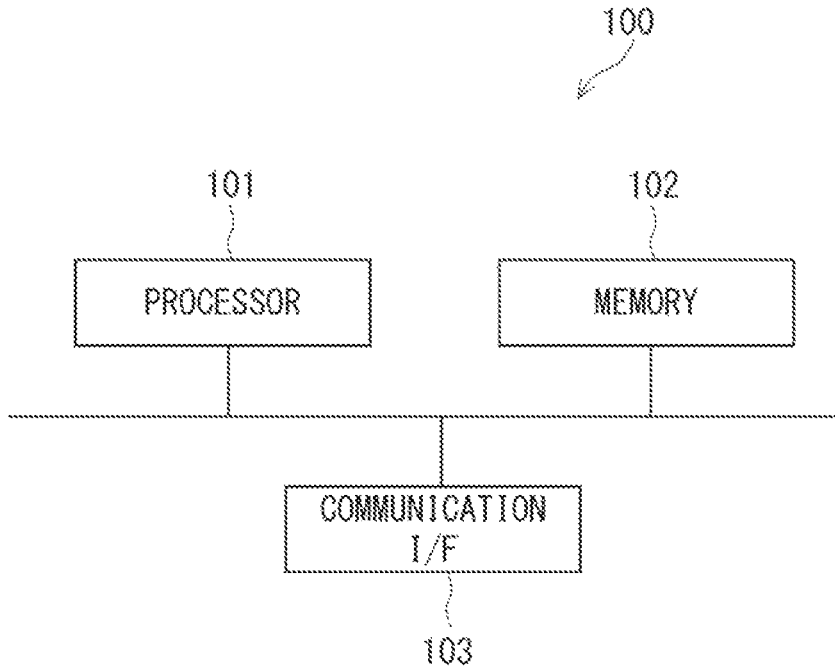

FIG. 3 is a block diagram illustrating a configuration example of an information processing apparatus in the information processing system in FIG. 2;

FIG. 4 is a diagram for explaining a notification example in a terminal apparatus in the information processing system in FIG. 2;

FIG. 5 is a schematic diagram for explaining an example of a flow of notification in the information processing system in FIG. 2;

FIG. 6 is a schematic diagram for explaining another example of the flow of notification in the information processing system in FIG. 2;

FIG. 7 is a flowchart for explaining an example of notification processing in the information processing system in FIG. 2;

FIG. 8 is a flowchart for explaining an example of notification processing in the information processing system according to a third example embodiment;

FIG. 9 is a schematic diagram illustrating a configuration example of an information processing system according to a fourth example embodiment; and FIG. 10 is a diagram illustrating an example of a hardware configuration of the apparatus.

EXAMPLE EMBODIMENT

Hereinafter, example embodiments will be explained with reference to the drawings. In the example embodiments, the same or equivalent elements may be denoted by the same reference numerals, and redundant explanation will be omitted as appropriate.

First Example Embodiment

Figure 1:
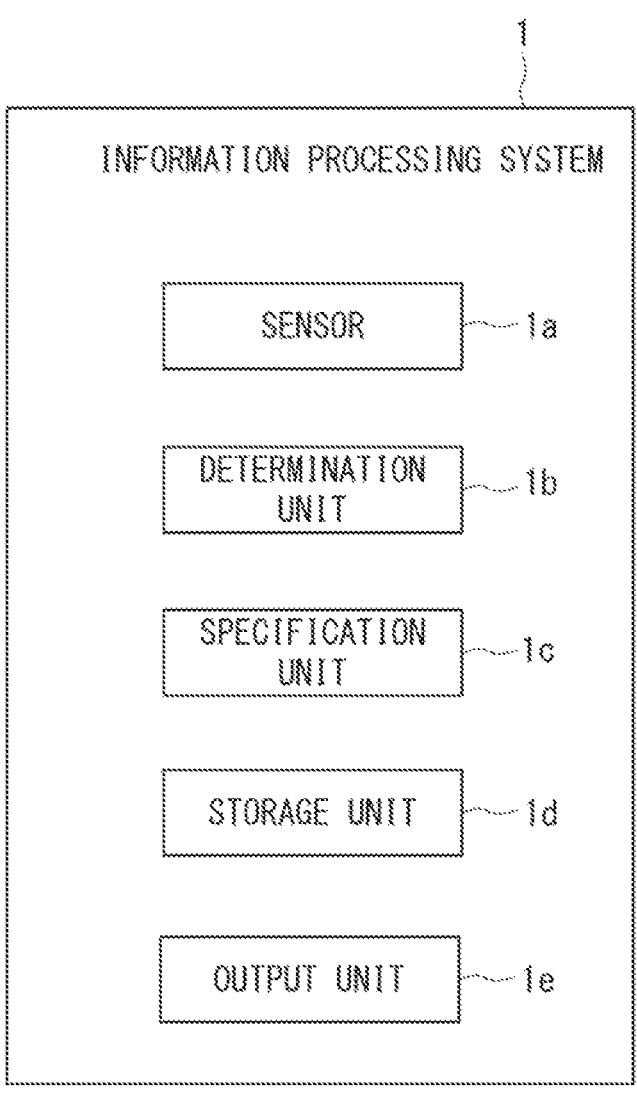
FIG. 1 is a block diagram illustrating a configuration example of an information processing system according to a first example embodiment.

FIG. 1 is a block diagram illustrating a configuration example of an information processing system according to a first example embodiment.

As illustrated in FIG. 1, an information processing system 1 according to the present example embodiment may include a sensor 1a, a determination unit 1b, a specification unit 1c, a storage unit 1d, and an output unit 1e.

The sensor 1a is a sensor that detects entry of a person into a room that is a watching target (monitoring target) for watching over a care recipient, and can be a human detecting sensor provided at a position where entry can be detected. A care recipient may also be referred to as a person to be assisted, a care receiver, a person required to be assisted, or the like. The caregiver may be a caregiver, a doctor, or the like, and may also be referred to as a helper.

Herein, examples of the room that is a monitoring target include a toilet, a bathroom, and the like. The information processing system 1 can be used in, for example, an elderly facility, an individual home, a hospital, or the like in a place where a care receiver needs to be watched over. Examples of the sensor 1a include an infrared sensor and an optical sensor. The sensor 1a is not limited to infrared rays or the like, and may be a sensor using any method such as image identification and ultrasonic waves. In addition, the sensor 1a is preferably configured to be able to detect the exit from the room after the entry to the room, and in a simple example, when a person is detected after the entry to the room is detected, the sensor 1a can detect the exit from the room.

The determination unit 1b determines whether the person who has entered the room is a care recipient as a user (user) of the room or a caregiver who provides care for the user.

The determination unit 1b can also be configured to determine whether a person who has exited the room is a care recipient or a caregiver.

The specification unit 1c specifies a person who has entered the room. Examples of the individual specification method in the specification unit 1c include various methods such as ecological authentication of a face, a pupil, and the like, and a method using a radio wave output apparatus that can be uniquely identified for each individual. In addition, the specification unit 1c can also be configured to specify a person who has exited the room. As the processing of specifying a person in the specification unit 1c, it is only necessary to specify (identify) an individual, and for example, face authentication processing can be applied, and in this case, the specification unit 1c, can also be referred to as an authentication unit.

The determination unit 1b and the specification unit 1c, may include a common component in some parts. The specification unit 1c, may include, for example, a human recognition sensor that includes a camera and a face authentication processor, a human recognition sensor, which recognizes a tag held by a person as part of clothing, an integrated circuit (IC) card, or the like and thereby performs person recognition, or the like. The determination unit 1b can use a recognition result and intermediate data in the human recognition sensor. In this way, the determination unit 1b can be included as part of the function of the specification unit 1c.

Based on the recognition result by the human recognition sensor, the determination unit 1b determines whether the person who has entered or exited the room is a care recipient or a caregiver, and the specification unit 1c, specifies the individual person. The determination itself can be executed by referring to information indicating a care receiver (a person who can be a care recipient) or a caregiver associated with the recognized person in advance. It is desirable that the determination unit 1b performs the determination without passing through processing that takes time for processing such as face authentication processing, and it is preferable to apply processing in which a load such as whether or not the person simply wears a uniform even when authentication processing of a camera image is used is light.

The user of the room can also assume a person who does not fall under any of the care recipient and the caregiver (e.g., a family member who has come to visit), but the determination unit 1b may determine that the person is not a care recipient or a caregiver in that case. Alternatively, the determination unit 1b may be configured to determine a person other than a caregiver as a care recipient because it is easier for the caregiver to apply a tag or the like for determination than the care recipient.

The storage unit Id is a storage apparatus that stores an entry detection result by the sensor 1a, a determination result by the determination unit 1b, and a specification result by the specification unit 1c. This storage may be performed until the output by the output unit 1e, which will be described later, is performed, or can be held as a log. In addition, the storage unit 1d can also store a notification destination, a notification condition to be described later in another example embodiment, and the like.

The output unit 1e outputs first notification information indicating the entry detection result, second notification information indicating the determination result, and third notification information indicating the specification result to the notification destination. The notification destination can be set in advance, and can be stored in the storage unit 1d, for example. The output unit 1e may be, for example, a communication unit configured by a wired or wireless communication interface or the like. The output unit 1e can transmit the notification information to a terminal apparatus (not illustrated) being the notification destination via a communication unit, for example. For example, the output unit 1e can transmit notification information to an external server (not illustrated) via the communication unit, and thus the server can transfer the notification information to the terminal apparatus being the notification destination.

Further, the information processing system 1 may include a control unit (not illustrated), and the control unit may include the determination unit 1b, the specification unit 1c, the storage unit 1d, and the output unit 1e (or a part thereof) which are described above. The control unit can be achieved by, for example, Central Processing Unit (CPU), a working memory, a non-volatile storage apparatus storing a program, and the like. This program can be a program for causing the CPU to execute processing of inputting a detection result from the sensor 1a and processing of the determination unit 1b, the specification unit 1c the storage unit 1d, and the output unit 1e. Further, the control unit included in the information processing system 1 can be achieved by, for example, an integrated circuit.

Further, the information processing system 1 according to the present example embodiment can be configured as a single information processing apparatus or as a plurality of apparatuses in which functions are distributed. In the latter case, each apparatus may include a control unit, a communication unit, a storage unit as necessary, and the like and the plurality of apparatuses may be connected as necessary by wireless or wired communication, thereby achieving a function as the information processing system 1 in cooperation with each other.

As described above, in the information processing system 1 according to the present example embodiment, it is possible to notify the caregiver of an entry status of the care receiver to the room to be watched and information for specifying an individual who enters the room. In addition, according to the present example embodiment, since the caregiver can understand a situation of the care receiver, it is not necessary to always watch. As a result, the caregiver can reduce the burden of watching, such as being able to go to another work. In addition, the caregiver can understand the situation of the care receiver, thereby enabling the caregiver to provide a generous support suitable for the person. In addition, the information processing system 1 may be referred to as an entry detection notification system because the system detects entry of a person into a room.

Second Example Embodiment

Although a second example embodiment will be mainly explained with reference to FIGS. 2 to 7 while focusing on a difference from the first example embodiment, various examples explained in the first example embodiment can be applied. FIG. 2 is a diagram illustrating a configuration example of an information processing system according to the second example embodiment.

The information processing system according to the present example embodiment (hereinafter, the present system) may be a system in which a part of the information processing system is installed in a toilet and notifies a caregiver or the like, and will be explained in detail below.

As illustrated in FIG. 2, the present system may include an information processing apparatus 60 attached to a toilet bowl 10, a server 40 wirelessly connected to the information processing apparatus 60, and a terminal apparatus 50 wirelessly connected to the server 40. Note that these may be connected in one wireless Local Area Network (LAN), for example. In addition, in the following explanation, it is assumed that the information processing apparatus 60 is installed in the toilet bowl 10 of the toilet and excretion information is also acquired, but the excretion information can be acquired as long as at least a part of the information processing apparatus is installed in the toilet bowl 10, such as a camera for capturing imaging data for acquiring the excretion information.

The toilet bowl 10 may include an edge 10c for forming a water retention portion with a side surface 10a, and may also include a planar portion 10b that is continuous from the edge 10c. The flat portion 10b may be provided with a toilet seat 11 including, for example, a toilet seat main body 11a equipped with a hot water cleaning function for user cleaning and the like, and a toilet seat cover 11b for closing the toilet seat main body 11a.

The information processing apparatus 60 can be a toilet-installed type (in this example, a toilet-installed type) apparatus, and notifies a detection event such as a detection event in which entry is detected, while cooperating with the server 40 and the terminal apparatus 50. Herein, an example in which the information processing apparatus 60 is an excretion information collection apparatus having a function of acquiring excretion information will be explained. In this case, an event related to excretion such as the start of the excretion or the end of the excretion can also be notified as a detection event. Although not explained in detail, the information processing apparatus 60 may be configured to record excrement, present excrement information (notification or the like), and predict excrement while cooperating with the server 40 and the terminal apparatus 50. The information processing apparatus 60 and the toilet bowl 10 can constitute, for example, a toilet bowl with a function of outputting excretion information.

In addition, a shape of the information processing apparatus 60 is not limited to the shape illustrated in FIG. 2, and may be configured such that the whole or a part of the function thereof is embedded in, for example, the toilet seat main body 11a or the like. In addition, a part of the functions of the information processing apparatus 60 may be provided on the toilet seat main body 11a side.

Before explaining a detailed example of the information processing apparatus 60, a configuration associated to each unit of the information processing system 1 in FIG. 1 will be briefly explained.

As illustrated in FIG. 2, the information processing apparatus 60 according to the present example embodiment is installed in the toilet bowl 10, and may include a human detecting sensor 24, an image capture apparatus 25, an information collection unit 26, a storage housing 61, a bridge portion 62, an inner housing 63, a control unit 67, a separate housing 68, and an outer housing 69.

The human detecting sensor 24 is an example of the sensor 1a, and is a sensor that detects a user (user) of the toilet bowl 10 of the toilet, and examples thereof include an infrared sensor and an optical sensor.

The image capture apparatus 25 is an apparatus that functions as a part of the specification unit 1c, and is an apparatus that captures an image of a face of a user of a toilet, and may be, for example, a camera (a camera for face authentication) that photographs a still image and/or a moving image. The image capture apparatus 25 is not limited to a visible light camera, and may be an infrared light camera or the like.

It is assumed that the information collection unit 26 is disposed in the inner housing 63. However, the information collection unit 26 is disposed in such a way that information can be collected from a reservoir portion of the toilet bowl 10 (an area where excrement is excreted), for example, by exposing an information collection surface of the information collection unit 26 from an opening of the inner housing 63. The information collection surface is relevant to, for example, a lens surface in a case of a camera and a detection surface in a case of a sensor.

The information collection unit 26 is a portion that collects information regarding excrement in the toilet bowl 10, and may be, for example, an image capture apparatus that collects contents of excrement such as a shape and a color of the excrement through an optical lens, a range sensor that optically measures a distance, or the like. The excretion information may be information indicating the contents of the excretion, and in a simpler example, may be information indicating that the excrement is feces (stool) or pee (urine). The excretion information may include other information, such as information indicating a color of excrement, and a shape of a solid body when excretion is the solid body. The information collection unit 26 may be configured to simply detect and collect the presence or absence of excretion as the information regarding the excrement.

The information collection unit 26 can set an area (excretion range) including a water retention portion of the toilet bowl as a collection range, and this excretion range can also be referred to as an excretion scheduled range. By installing the information collection unit 26 in such a way as to include such an excretion range in an imaging range, excrement and the like are included as a subject in the imaging data to be captured. Of course, it is preferable that the above-described excretion range is a range in which a user is not reflected, and it is preferable that the information collection unit 26 is installed in such a way that the lens or the like is not visible to the user. Further, the information processing apparatus 60 includes the information collection unit 26, and thus can also be referred to as a toilet sensor.

The information collection unit 26, the human detecting sensor 24, and the image capture apparatus 25 are connected to the control unit 67 by wired or wireless communication. Note that FIG. 2 illustrates an example in which the information collection unit 26 is connected to the control unit 67 by a cable K1, and the human detecting sensor 24 and the image capture apparatus 25 are connected to the control unit 67 by a cable K2.

The control unit 67 controls the human detecting sensor 24, the image capture apparatus 25, and the information collection unit 26. For example, the control unit 67 can receive a detection result by the human detecting sensor 24, can instruct the image capture apparatus 25 to capture an image, can receive an image captured, can instruct the information collection unit 26 to collect information regarding excrement, and can receive collected information. In addition, the control unit 67 can be configured to execute functions of the determination unit 1b and the specification unit 1c together with the image capture apparatus 25. The control unit 67 may include a storage apparatus associated to the storage unit 1d.

The control unit 67 can be achieved by, for example, a CPU, a working memory, a nonvolatile storage apparatus storing a program, or the like. This program can be, for example, a program for causing the CPU to execute the above-described processing. The control unit 67 can also be achieved by, for example, an integrated circuit.

The storage housing 61 is a housing that stores the control unit 67 and that is arranged outside the toilet bowl 10, and is hereinafter explained as a control box 61. The bridge portion (crossover) 62 is a portion that bridges the inner housing 63 and the outer housing 69. In short, the crossover 62 is installed at the edge 10*c* of the toilet bowl 10 by a mechanism that connects the inner housing 63 and the outer housing 69. The outer housing 69 is a housing including a clamp mechanism for fixing the inner housing 63 and the toilet bowl 10. The outer housing 69 is a housing arranged outside the toilet bowl 10 and may be in any shape as long as it does not interfere with excretion.

The above-described clamp mechanism (fixing clamp mechanism) can be a mechanism that fixes the inner housing 63 and the outer housing 69 to the edge 10*c* by, for example, adjusting and holding a distance from an inner side of the edge 10*c* via the crossover 62. Accordingly, the inner housing 63 of the information processing apparatus 60 can be securely fixed and installed regardless of the shape of the toilet bowl 10 such as the shape of the edge 10*c*. Further, the shape and components of the fixing clamp mechanism are not limited as long as the mechanism is such. The fixing clamp mechanism may be provided with its main components in the outer housing 69.

The inner housing 63 is a housing in which the information collection unit 26 is disposed, and is hereinafter explained as a sensor box 63. The sensor box 63 is provided with, for example, an optical sensor for collecting the information regarding the excrement, and is arranged inside the toilet bowl 10.

A separate housing 68 is a housing in which the human detecting sensor 24 and the image capture apparatus 25 are disposed. The separate housing 68 includes a human detecting sensor 24 for human detection and an image capture apparatus (camera) 25 for face authentication disposed inside or partially outside, and is hereinafter explained as a human detection/identification box 68. In addition, a human detection/identification box 68 may be provided with a camera adjustment mechanism that adjusts a direction of the camera in the horizontal direction. The image capture apparatus 25 may expose, for example, a lens from the human detection/identification box 68 in such a way as to be able to capture an image of the face of the user of the toilet, but may only photograph the face. In addition, the human detecting sensor 24 may expose a detection surface from the human detection/identification box 68 in such a way as to be able to detect the user of the toilet, but it is only necessary that the person be able to detect. When the human detecting sensor 24 and the image capture apparatus 25 are connected to the control unit 67 by wired or wireless communication, information can be transmitted and received.

The human detection/identification box 68 may be disposed at a position spaced apart from the control box 61 and the toilet bowl 10, as illustrated in FIG. 2. FIG. 2 illustrates an example in which the human detection/identification box 68 is installed on a wall W of the toilet in which the toilet bowl 10 is installed. The human detection/identification box 68 can adopt a wired connection or a wireless connection with the control box 61 by the cable K2, and can be used at a position away from the control box 61 in any case. The human detection/identification box 68 can be horizontally rotated and provided with a mechanism for fixing an orientation of the rotating box.

In addition, it is preferable that the human detecting sensor 24 is disposed in such a way that the detection surface is positioned at least at a position higher than the crossover 62, and the image capture apparatus 25 is disposed in such a way that an imaging lens is positioned at least at the position higher than the crossover 62, in order to facilitate detection and imaging of a person. Further, it is more preferable to provide the detection surface and the imaging lens at a position higher by a predetermined height in consideration of the height of the toilet seat 11.

In the configuration of the information processing apparatus 60 illustrated in FIG. 2, the human detection/identification box 68, the control box 61 having the control unit 67, and the sensor box 63 having the excretion information collection function are connected by the cables K1 and K2. However, the human detection/identification box 68 is disposed on the wall W of the toilet, and the box having control unit 67 is arranged on a side surface of the toilet bowl 10, and the installation work thereof is also easy. In addition, the control box 61 may be arranged on a rear surface side of the toilet bowl 10, and the installation work in this case is also easy. In addition, it is desirable that each of the cables K1 and K2 includes a power supply line for supplying power from the control box 61. Power is supplied to the control box 61 from a power cable which is not illustrated.

In FIG. 2, although it is assumed that the cable K1 passes through the inside of the crossover 62, the cable K1 is connected to the information collection unit 26, is derived from the sensor box 63, it is also possible to be directly connected to the control box 61. In this case, the cable K1 passes through an upper surface side of the edge 10*c* of the toilet bowl 10 (passes between the upper surface of the edge 10*c* and the toilet seat main body 11*a*).

The server 40 may include a control unit 41 that controls the entirety of the server, and a storage unit 42 that stores a notification condition and various acquired information (and information generated based on the information). In addition, the control unit 41 can be configured to execute the functions of the determination unit 1*b* and the specification unit 1*c* together with the image capture apparatus 25. The control unit 41 may be configured to execute the function of the output unit 1*e* in FIG. 1.

The control unit 41 can be achieved by, for example, a CPU, a working memory, a nonvolatile storage apparatus storing a program, and the like. The control unit 41 can also be achieved by, for example, an integrated circuit. This storage apparatus can also serve as the storage unit 42, and this program can be a program for causing the CPU to achieve the functions of the server 40.

Further, the storage unit 42 can function as the storage unit 1*d*. Further, the storage unit 42 can store, as notification conditions, notification information (first, second, and third notification information) and a notification destination in a case where the necessity of notification and the notification are necessary for each person to be assisted as the user. Thus, the server 40 having the function of the output unit 1*e* can output to the notification destination in accordance with the notification condition. In addition, the storage unit 42 can also store, as the notification conditions, notification information (first, second, and third notification information) and a notification destination in a case where the necessity of the notification and the notification are necessary for each detection event and for each person to be assisted as the user. Thus, the server 40 having the function of the output unit 1*e* can output to the notification destination in response to the occurrence of the detection event in accordance with the notification condition. The number of notification destinations to be notified to a certain detection event may be one, or may be a plurality.

Further, the server 40 preferably includes a setting unit that sets a notification condition from external equipment such as the terminal apparatus 50, and thereby can set a notification condition according to an operation mode.

The terminal apparatus 50 is a terminal apparatus possessed by a caregiver who provides care for (will provide care for) a care recipient as a user of a toilet, and can be a portable information processing apparatus, but may be an installation type apparatus. In the former case, the terminal apparatus 50 may be a smart device such as a mobile phone (also referred to as a smartphone), a tablet, or a mobile PC, or may be an electric bulletin board or the like. Although not illustrated, the terminal apparatus 50 can also include a control unit that performs overall control and a storage unit, and the control unit can be achieved by, for example, a CPU, a working memory, a storage apparatus, or the like, as with the control unit 41. The program stored in the storage apparatus can be a program for causing the CPU to achieve a function of the terminal apparatus 50.

Next, a detailed example of the information processing apparatus 60 will be explained with reference to FIG. 3. FIG. 3 is a block diagram illustrating a configuration example of an information processing apparatus in the information processing system in FIG. 2. For example, the information processing apparatus 60 may be configured by two apparatuses as illustrated in FIGS. 2 and 3. Further, since the information processing apparatus 60 includes various sensors installed in the toilet, it can also be referred to as a "toilet sensor" or a "toilet sensor apparatus". The toilet sensor is relevant to a so-called edge in the present system in which the monitoring of the use of the toilet by the care recipient is performed via the communication network.

For example, a CPU 27a, a connector 27b, USB I/F 27c, a WiFi module 27e, and a Bluetooth module 27f can be stored in the control box 61. Note that USB is an abbreviation for Universal Serial Bus, and USB, WiFi, and Bluetooth are all registered trademarks (the same applies hereinafter). The connector 27b is connected to a range sensor 26a, the human detecting sensor 24, and the image capture apparatus (second camera) 25. Note that the control box 61 does not include various I/Fs and connectors, and can be directly connected to the CPU 27a. In addition, the information processing apparatus 60 is not equipped with the CPU 27a, and it is also possible to only include sensors and cameras that acquire various data and a function of transmitting various data to the server 40 side.

As illustrated in FIG. 3, the control box 61 and the sensor box 63 are connected by interfaces exemplified by the connector 27b and USB I/F 27c, and a connection line thereof is accommodated in the cable K1. A part of the cable K1 passes through the inside of the crossover 62 (and the outer housing 69). In addition, the control box 61 and the human detection/identification box 68 are connected by an interface exemplified by the connector 27b, and a connection line thereof is accommodated in the cable K2.

As described above, in the information processing apparatus 60, the boxes and the cross 62 are provided with a substrate, a cable for connecting them, and the like. The information processing apparatus 60 adopts the above-described divided box configuration and optimizes a direction of the connector to which the cable is connected, thereby reducing the space required for an extra cable length and reducing sizes of the substrate and the mounted components. Further, in the present example embodiment, the lateral width of each structure can be suppressed by dividing the arrangement locations of the boxes.

The sensor box 63 can store, for example, the range sensor 26a that functions as a sitting sensor that detects that the user is sitting on the toilet seat 11, and a first camera 26b that photographs excrement.

Next, components in each box will be explained.

The CPU 27a is an example of a main control unit of the information processing apparatus 60 and controls the entire information processing apparatus 60. The connector 27b connects the human detecting sensor 24, the second camera 25, the range sensor 26a, and the CPU 27a. The USB I/F 27c connects the first camera 26b and the CPU 27a.

The range sensor 26a is a sensor that measures a distance to an object (buttocks of a user of the toilet bowl 10) and detects that a user is sitting on the toilet seat 11, and detects that the object is sitting on the toilet seat 11 when a certain period of time has elapsed beyond a threshold value. Further, the range sensor 26a detects that the user has left the toilet seat 11 when there is a change in the distance to the object after sitting.

As the range sensor 26a, for example, an infrared sensor, an ultrasonic sensor, an optical sensor, or the like can be employed. When the range sensor 26a employs an optical sensor, a transmitting and receiving element may be arranged in such a way that light (not limited to visible light) can be transmitted and received from a hole provided in the sensor box 63. The transmitting and receiving element may be configured separately from the transmitting element and the receiving element, or may be integrated with each other. The range sensor 26a is connected to the CPU 27a via the connector 27b, and can transmit the detection result to the CPU 27a side. Based on the detection result, the CPU 27a can acquire leaving/sitting data indicating leaving/sitting information regarding the person, and can transmit the data to the server 40 side via the WiFi module 27e.

The first camera 26b is an example of a camera that captures image data that are a source of acquisition of excretion information, and may be an optical camera in which a lens portion is arranged in a hole provided in the sensor box 63. The first camera 26b is installed in such a way as to include the excretion range of excrement in the toilet bowl 10 of the toilet in the imaging range. The first camera 26b is connected to the CPU 27a via the USB I/F 27c, and transmits the captured image data to the CPU 27a side.

The human detecting sensor 24 is an example of the sensor 1a, and is a sensor that detects presence of a person (entry/exit of a person) in a specific area (a measurement area range of the human detecting sensor 24) that is a part of a room of the toilet, and can be referred to as an entry/exit sensor. As the human detecting sensor 24, for example, an infrared sensor, an ultrasonic sensor, an optical sensor, and the like can be adopted regardless of the detection method. The human detecting sensor 24 is connected to the CPU 27a via the connector 27b, and transmits a detection result to the CPU 27a when a person is detected in a specific area. The detection result can be transmitted by the CPU 27a to the server 40 via the WiFi module 27e.

The second camera 25 may be an optical camera, and is an example of a camera that photographs a face image of a user and acquires face image data in order to identify the user of the toilet. The second camera 25 can be installed in a room of a toilet in which the toilet bowl 10 is installed. As described above, the second camera 25 can also be used as a part of the determination unit 1b and the specification unit 1c in FIG. 1, and authentication of a person can be performed by carrying out face authentication processing using face image data captured by the second camera 25. In the present system, when the human detecting sensor 24 detects a person, it is also possible to perform processing such that the second camera 25 photographs a target person who has entered the toilet. Thus, the face authentication can be carried out only when a person is detected.

The Bluetooth module 27f is an example of a receiver that receives identification data for identifying a user from a Bluetooth tag held by the user, and may be replaced with a module based on another short-distance communication standard. The Bluetooth tag to be held by the user can be held by the user, for example, by embedding the Bluetooth tag in a wristband or the like as a different ID for each user. As described above, the Bluetooth module 27f can be used as a part of the specification unit 1c in FIG. 1, and can authenticate a person, based on the received identification data. As described above, in the configuration example of FIG. 3, two of the second camera 25 and the Bluetooth module 27f are provided as a function of acquiring information for person authentication (individual specification).

The WiFi module 27e is an example of communication equipment that transmits various acquired data to the server 40, and may be replaced with a module that adopts another communication standard. The face image data acquired by the second camera 25 and the identification data acquired by the Bluetooth module 27f can be transmitted by the CPU 27a to the server 40 via the WiFi module 27e.

The CPU 27a, the USB I/F 27c, the WiFi module 27e, and the server 40 acquire excretion information, based on the imaging data captured by the first camera 26b. In this case, the server 40 may be responsible for main processing of acquiring the excretion information from the imaging data. The server 40 in the example in FIG. 2 inputs the imaging data into a learned model, for example, and acquires the excretion information. Then, the server 40 preferably mainly acquires, as a part of pieces of the excretion information, information indicating whether or not a foreign body that is an object other than feces and urine is included in the imaging data as a subject excluding the toilet bowl and washing liquid for the toilet bowl. The foreign body can be referred to as another object, may be a liquid or a solid as long as other than feces and urine, and can include, for example, any one or a plurality of vomit, melena, vomiting of blood (hematemesis), a diaper, a urine absorbing pad, a toilet paper core, and the like. In addition, the server 40 can be configured to acquire a shape, color, and amount of excrement as the excrement information when there is not a foreign body but excrement.

The CPU 27a, the WiFi module 27e, the server 40, and the terminal apparatus 50 can be one example of the output unit 1e in FIG. 1. In this case, the server 40 can be responsible for main processing of detecting, from, including an entry detection result, a determination result, and a specification result (an authentication result), excretion information and leaving/sitting information, a detection event indicated by the entry detection result, the determination result, the specification result (authentication result), the excretion information, and the leaving/sitting information. Further, in this case, the terminal apparatus 50 can be responsible for the main processing of outputting notification information, and the terminal apparatus 50 receives the notification information transmitted from the server 40, and notifies the received notification information by display and/or audio output. Further, although the terminal apparatus 50 is explained on the assumption that it is a smart device, the terminal apparatus 50 may be an apparatus that only emits a sound at the time of receiving a notification, an electronic bulletin board that displays an entry, a personal name, or the like.

Further, the server 40 may store information such as an entry detection result, a determination result, an authentication result, excretion information, and leaving/sitting information in the storage unit 42 or the like, and the server 40 may output the information in response to access from the terminal apparatus 50, for example. In particular, it is desirable that the server 40 has a function of generating an excretion diary, and in this case, by storing the generated excretion diary in the storage unit 42, the excretion diary can be viewed from the terminal apparatus 50 when a caregiver who is a user of the terminal apparatus 50 desires. Note that, although the excretion diary includes a date and time of excretion behavior, the date and time can be acquired by any one of an imaging date and time of imaging data, an identification date and time of a subject, an entry and exit date and time, a sitting date and time, a leaving date and time, and a date and time in a middle of the sitting and leaving, and the like.

The server 40 receives the face image data acquired by the second camera via the WiFi module 27e, performs face authentication processing by comparing authentication data stored in advance with, for example, a feature point thereof and the like, and acquires identification data associated with matched authentication data. In this way, the server 40 can acquire identification data (identification data for identifying a user), i.e., determine whether the user is a caregiver, and specify the user.

Then, the server 40 can acquire face image data of a user (care recipient) of the toilet bowl 10 or a caregiver at a time of acquiring imaging data together with the imaging data from the information processing apparatus 60. Therefore, for example, the control unit 41 of the server 40 can identify a person who has entered the room, based on the face image data, and can also determine whether to be matched with the notification condition stored in the storage unit 42 by using identification information regarding the person as a key. Note that, it is preferable that the face image data captured by the second camera 25 is not stored in consideration of privacy.

Further, the server 40 receives identification data (personal authentication data) acquired by the Bluetooth module 27f via the WiFi module 27e, and performs user authentication by comparing with authentication identification data stored in advance. Note that, for example, even when a caregiver holding his/her Bluetooth tag and a care recipient holding his/her Bluetooth tag enter a toilet together, the both can be distinguished and recognized with each other. In this way, the server 40 can acquire a result acquired by determining whether or not the person entering the toilet is a caregiver and identification data of the person. Then, the control unit 41 of the server 40 can determine whether to be matched with the notification condition stored in the storage unit 42 by using the identification data as a key.

Note that, in this example, it can be said that a care recipient and a caregiver are specified from two types of data, that are face image data and identification data, and two specification functions are provided, but needless to say, the care recipient and the caregiver can be specified by either one. For example, the present system provides both specification functions, and can select one of them at a time of operation. Alternatively, the present system can provide only one of the specification functions.

As described above, a detection result by the human detecting sensor 24 can be transmitted to the server 40. Since the detection result can be used for determining entry/exit to/from the toilet, the server 40 can acquire exit information indicating the exit even when there is no detection, or when the detection is performed again. When the detection result is received from the information processing apparatus 60, the server 40 stores, in the storage unit 42 or the like, data (entry/exit data) indicating the entry/exit to/from the toilet, which is an installation location of the toilet bowl 10 in association with the identification data of the specified user as described above. Note that the entry/exit data can also include identification data.

Then, the control unit 41 of the server 40 compares the authentication result of a person indicated by the received identification data, entry/exit information indicated by the entry/exit data, the leaving/sitting information indicated by the leaving/sitting data, and excretion information indicating the start and end of the excretion with the notification condition stored in the storage unit 42. As a result of this comparison, when there is a matching notification condition, the control unit 41 outputs notification information indicated by the notification condition to a notification destination indicated by the notification condition. In the following, for the sake of simplification of the explanation, a notification based mainly on information indicating an entry detection result, a determination result, and a specification result will be explained in connection with the notification. However, the present system may be configured to notify information relating to various types of detection results as described above.

The notification destination can be the terminal apparatus 50 held by any one or a plurality of helpers, and which helper is the notification destination is included in the notification condition. Note that the notification destination may be, for example, a notification apparatus of a nurse call system, another terminal apparatus (for example, personal handy-phone system (PHS)) possessed by a caregiver other than the terminal apparatus 50, an intercom, or the like, in addition to or in place of the terminal apparatus 50.

In particular, in the present example embodiment, after the first notification information indicating the entry detection result by the human detecting sensor 24 and the second notification information indicating the determination result are output to the notification destination, the third notification information indicating the specification result of the person who has entered the room is output to the notification destination. In short, the server 40 notifies the notification destination of occurrence of the detection event indicating that the care recipient has entered the room, and then notifies the notification destination of the occurrence of the detection event indicating that the person has been able to be specified. Timings of these notifications can also be stored as the above-described notification conditions. As a result, the caregiver can rush to the toilet when the care recipient has entered the room without waiting for specification of the care recipient. In the present example embodiment, only when it is determined that the determination result is a care recipient, it is also possible to execute person specification processing such as person authentication processing.

In addition, the server 40 may include a setting unit (not illustrated) that sets a notification condition from the terminal apparatus 50 or the like. The setting unit can be mounted as a part of the function of the control unit 41, and accepts a change operation such as addition, correction, or deletion of the notification condition from the terminal apparatus 50 or the like, and changes the notification condition stored in the storage unit 42 according to the change operation.

In addition, the notification condition may include a condition indicating that, when it is detected that a caregiver who provides care for a care recipient has entered the room before the care recipient as the user enters the room, the care recipient and the caregiver do not notify (suspend the notification) until the care recipient and the caregiver are no longer in the room after that. As a result, it is possible to prevent another caregiver from rushing along with the entry of the care recipient.

In addition, the notification condition may include a condition indicating that no notification is made while a caregiver, who provides care for a care recipient, as the notification destination is in the room in a state in which the caregiver as the user is in the room. As a result, it is possible to prevent another caregiver from rushing.

Next, a display example of notification information to the terminal apparatus 50 will be explained with reference to FIG. 4. FIG. 4 is a diagram for explaining a notification example in the terminal apparatus in the information processing system in FIG. 2.

As illustrated in FIG. 4, the terminal apparatus 50 can notify notification information 52 to 54 in that order on the display screen 51. The notification information 52 is an example of notification information that is first notification information and second notification information for detecting a person by the human detecting sensor 24 and when the person is a care recipient, notifying that the care recipient enters the toilet.

The notification information 53 notified after the notification information 52 is an example of the third notification information that detects a person by the human detecting sensor 24, determines whether the user is a caregiver or a care recipient, then identifies the user, and notifies that the person who has entered the room is a user of the room (a care recipient, Mr./Mrs. PA in this example).

The identification of the user can be acquired as a result of performing the face authentication processing based on the face image data acquired by the second camera 25 or the identification processing received by the Bluetooth module 27*f* when a person is detected by the human detecting sensor 24. By recording a care receiver who needs care with a plurality of persons in a face authentication person list or an identification person list, when a detected person is the person, the notification information 53 can include information notifying that the person is a target person who needs care with a plurality of persons next to a name (Mr./Mrs. PA in this example). In addition, it is possible to add information (not illustrated) including a mark indicating importance to the notification information 53, and also include a button (not illustrated) for selecting to notify that the user handles the care receiver.

In addition, when it is detected that Mr./Mrs. PA has exited the room, notification information 54 indicating that Mr./Mrs. PA has exited the room can be displayed.

Next, a more specific example of the notification processing will be explained with reference to FIGS. 5 and 6. FIG. 5 is a schematic diagram for explaining an example of a notification flow in the information processing system of FIG. 2. FIG. 6 is a schematic diagram for explaining another example of the notification flow in the information processing system in FIG. 2.

As illustrated in FIG. 5, as for the toilet bowl with the information processing apparatus 60, in the human detection/identification box 68 including the human detecting sensor 24 that functions as an entry sensor and the second camera 25, the human detecting sensor 24 detects that a person has entered the toilet. When detecting that a person has entered the room, the information processing apparatus 60 transmits the detection result to the server 40. As illustrated in FIG. 5, the server 40 may be a cloud server. Further, the information processing apparatus 60 determines whether the person is a care recipient or a caregiver, and transmits the determination result to the server 40. Note that this determination can also be performed on the server 40 side, and in this case, the information processing apparatus 60 may transmit information that serves as a determination material to the server 40. Further, the information processing apparatus 60 transmits the image data acquired by the second camera 25 to the server 40.

The server 40 receives the entry notification and the determination result, and transmits the entry notification to the terminal apparatus 50 such as a smartphone of a caregiver C in a place away from the toilet. At the same time, the server 40 executes authentication processing for specifying an individual from the received image data, and transmits information indicating the specified person as a result of the authentication to the terminal apparatus 50.

In addition, when the range sensor 26a that functions as a siting sensor detects that the user is sitting on the toilet seat 11 of the toilet, the information processing apparatus 60 transmits a sitting notification to the server 40, and starts imaging by the first camera 26b and transmits face image data to the server 40. In response to the sitting notification, the server 40 determines that the user is a care recipient, based on the information acquired by the entry/exit sensor, analyzes the received imaging data, and, upon detecting the start of excretion, can transmit an excretion start notification to the terminal apparatus 50 of the caregiver C.

In addition, the server 40 can also transmit an excretion end notification to the terminal apparatus 50 of the caregiver C when the excretion completion is detected from the imaging data. The information processing apparatus 60 can also transmit a leaving notification to the server 40 at the time of leaving the seat and an exit notification to the server 40 at the time of exiting the room, based on the detection results of the sitting sensor and the entry/exit sensor. The server 40 that has received the leaving notification and the exit notification can transmit the received notification to the terminal apparatus 50 of the caregiver C. As a result, the caregiver C is released from a constant attendance status at a time of excretion of the care recipient, and can rush or the like in an emergency (for example, in a case where there is no leaving notification for a long time) as necessary.

The present system can also be configured as illustrated in FIG. 6. FIG. 6 illustrates an example of notification processing in an example in which the present system is configured to specify a person who has entered the room by using an IC tag 80.

The system illustrated in FIG. 6 can include an information processing apparatus 60, a server 40 that is a cloud server, a terminal apparatus 50 such as a smartphone, and a radio wave output apparatus that can be uniquely identified for each individual. The information processing apparatus 60 and the terminal apparatus 50 are connected to the server 40 via a network N. The network N may be, for example, a Wi-Fi network, an LTE network, or the like.

The above-described radio wave output apparatus may be, for example, an IC tag 80a such as a radio frequency identifier (RFID) or near field communication (NFC), or a terminal apparatus 50a such as a smartphone including an IC tag. The terminal apparatus 50 functions as an apparatus that is owned by a caregiver and receives a notification, but also functions as a radio wave output apparatus including an IC tag. The caregiver can also own the IC tag 80 separately in a form of being included in a nameplate or the like.

In the IC tag, individual information for specifying an owner can be stored, whereby an individual can be specified, i.e., the individual can be identified by radio waves. However, in this example, since an individual can be specified from the image data acquired by the second camera 25, it is not essential to store individual information or to read the individual information. For example, the IC tag may store only information that indicates whether the individual is a caregiver (e.g., an employee in a facility) or not (e.g., is a visitor), or may read only such information.

The information processing apparatus 60 includes a human detection/identification box 68 installed at a place where entry detection and individual identification are performed, and a control box 61 having a communication function of transmitting information to the server 40 and a function of receiving radio waves from the IC tags 80a and 80 (i.e., radio wave receiving equipment). The radio wave receiving equipment may be an IC tag reader.

However, a set of the radio wave output apparatus and the radio wave reception apparatus to be used for determining whether or not the person is a caregiver, or identifying whether or not the person is a caregiver and individual identification, is not limited to a set of the IC tag and the IC tag reader. The radio wave output apparatus and the radio wave reception apparatus may be configured to transmit and receive radio waves in a system such as Bluetooth, Bluetooth Low Energy (BLE), or Ultra Wide Band (UWB). Further, the radio wave output apparatus may be a terminal apparatus 50 such as a smartphone without an IC tag as long as it can transmit and receive radio waves. Note that the above-described radio wave reception apparatus can also be provided in the human detection/identification box 68 as exemplified by the Bluetooth module 27f.

The human detection/identification box 68 includes the human detecting sensor 24 and the second camera 25 as described above. The human detecting sensor 24 is used for detecting the presence of a person in a specific area, and the second camera 25 is used for specifying a person (identifying an individual). As a method of determining whether or not the person is a caregiver and identifying an individual, it is also possible to authenticate ecological information such as a face and a pupil, based on data acquired by the second camera 25, a dedicated scanner, or the like.

In the system illustrated in FIG. 6, the information (the entry detection result, the image data, etc.) acquired by the human detection/identification box 68 is transmitted to the server 40, and the notification information is notified from the server 40 to the terminal apparatus 50 being the notification destination in real time. However, as described above, first, the first notification information and the second notification information are notified, and then the third notification information is notified.

Next, with reference to FIG. 7, a flow in which a notification is made by using an entry of a care receiver as a trigger in the present system will be explained. FIG. 7 is a flowchart for explaining an example of notification processing in the information processing system in FIG. 2. The processing in the information processing apparatus 60 is mainly executed by the CPU 27a, and the processing in the server 40 is mainly executed by the control unit 41. Herein, the flow will be explained based on the system of FIG. 6 as an example.

First, the information processing apparatus 60 monitors whether or not there is a reaction of the human detecting sensor 24 functioning as an entry sensor (step S1), and determines whether or not an entry of a caregiver has been detected in a stage where there is a reaction (a stage where YES in step S1) (step S2). In a case of NO in step S1, i.e., in a case where there is no response from the human detecting sensor 24, the information processing apparatus 60 waits until there is no response from the human detecting sensor 24.

When the care receiver enters the toilet, YES is acquired in step S1, and thereafter, the information processing apparatus 60 determines whether or not the caregiver has entered the room (i.e., whether or not the caregiver has been detected) by the equipped radio wave receiving apparatus (step S2). When determining that the person who has entered the room is a caregiver (YES in step S2), the information processing apparatus 60 ends the processing. On the other hand, when the caregiver is not detected (NO in step S2), the information processing apparatus 60 notifies the server 40 that the care recipient has entered the room via the network N (transmits the first notification information and the second notification information) (step S3). When a care recipient is detected in a configuration in which the care recipient can be detected, step S3 may be similarly executed.

Upon receiving the notification, the server 40 transmits, to the terminal apparatus 50, a notification indicating that the care receiver has entered the toilet. As a result, the terminal apparatus 50 can notify that the care receiver has entered the room. This allows the caregiver to confirm the notification and prepare for rushing. In short, such an entry notification allows the caregiver to know whether or not the person is in the room in order to prepare for confirmation, such as rushing.

After step S3, person authentication processing (individual identification processing) is performed (step S4). In the person authentication processing, the information processing apparatus 60 transmits the image data acquired by the second camera to the server 40 via the network N, and the server 40 performs authentication, based on the image data. However, the transmission itself can be performed immediately after the transmission of the first notification information and the second notification information in step S3. As a result of the authentication, the server 40 determines whether or not the person is registered as a care receiver (step S5). In step S5, when the person is registered, specification of the individual (person) is also performed.

In a case of YES in step S5 (in a case where the person is a registered person), the server 40 notifies the terminal apparatus 50 serving as a notification destination in the case of that person together with information indicating the person (step S6), and ends the processing. As a result, the caregiver can make a preparation and an action suitable for the person, and a person in charge of the person can also rush thereto. For example, a caregiver can know who has entered the room, and thus, the caregiver can rush when the care receiver needs assistance and when assistance is unnecessary, the caregiver can do other works without rushing.

On the other hand, in a case of NO in step S5 (in a case of a non-registered person), the server 40 notifies the terminal apparatus 50 serving as the notification destination in that case together with information indicating the person (step S7), and the processing is ended. As a result, the caregiver can make a preparation and an action suitable for the non-registered person, and a person in charge of the non-registered person can also rush thereto. With these functions, it is possible to solve the problems of watching over and assisting the care receiver, and therefore, it is possible to reduce a burden on the caregiver and to provide a generous support to the care receiver.

The above explanation has been given on the assumption that only one toilet bowl 10 (only one toilet room) exists for the present system. However, in the present system, it is preferable to acquire an entry detection result, an authentication result, and the like for detection of a detection event with regard to a plurality of toilets. This allows the present system to be applied even when a person to be assisted may use two or more toilets.

In addition, in a case of ta facility such as a hospital, the server 40 can be installed in the facility or can be installed in a private house or in an apartment house in a case of personal use. In either case, the server 40 may be a cloud server as described above.

In addition, the program of the terminal apparatus 50 can be incorporated in the terminal apparatus 50 in such a way as to be executable as care software including a notification function of the notification information. In addition to the notification information, the terminal apparatus 50 may also directly (or directly and automatically) receive and store information acquired on the toilet side of the information processing apparatus 60 or the like, and may also receive and store various kinds of information recorded in the server 40 in the same manner.

Of course, also in the present example embodiment, the information processing apparatus 60 alone can be configured to notify the terminal apparatus 50 by providing the function described as the function of the server 40 on the information processing apparatus 60 side without using the server 40. In short, it is also possible to adopt a configuration in which the information detected by the information processing apparatus 60 is directly notified to the terminal apparatus 50 possessed by the caregiver. In this case, it is possible to directly notify by using, for example, Bluetooth or ZigBee (registered trademark), or to notify by using a communication network using, for example, Wi-Fi or LTE.

As described above, in the present system, it is possible to watch over a care receiver, based on the information acquired by the information processing apparatus 60 relevant to a so-called edge of the communication network in a care facility or a residence. For example, when the information processing apparatus 60 is installed in a toilet in which entry detection is desired, it is possible to notify the terminal apparatus 50 of entry after the entry is detected by the human detecting sensor 24 and whether or not the person is a caregiver is determined. This notification can be executed only when the person is a care recipient, or can be executed by indicating whether the person is a caregiver or a care recipient in both cases. Thereafter, in the present system, the person information registered in advance can be used for the person and perform individual identification, and the person who has entered the room can be specified based on the result of the individual identification, and the specified person can be notified to the terminal apparatus 50.

In the present system, by the above-described configuration, the burden on the caregiver to monitor the toilet is reduced, and it is possible to provide a generous support to the care recipient. Specifically, the first to fourth problems can be solved as follows.

First, the first problem can be solved as follows. In the present example embodiment, when the human detecting sensor 24 detects a person, the terminal apparatus 50 is notified, and the caregiver can immediately know the entry. After that, it is possible to know who has entered the room by the individual identification, and it is not necessary to always watch over the care receiver. As a result, it is possible to solve the problem that the time required for the caregiver to monitor the care recipient is long.

The second problem can be solved as follows. The processing according to the present example embodiment is started by the human detecting sensor 24 detects a person, and ends when the individual identification is completed and then notified. As a result, it is not always monitored by the camera like a watching camera, and the privacy problem can be solved. In addition, since only target face and pupil are detected in ecological authentication of the face, the pupil, and the like, privacy can be protected. Accordingly, the present invention can be used for watching over a care receiver even in a privacy space, and the burden on the caregiver can be reduced.

The third problem can be solved as follows. In the present example embodiment, the caregiver can know the person who is in the room by the ecological authentication of the face, the pupil, or the like, or the person specification notification by the identification processing of the radio wave apparatus such as the Bluetooth tag or the smart device. As a result, it is possible to solve the problem that, since it is not known who has entered the room, wasteful labor is required, such as going to the site for confirmation once and providing assistance when assistance is necessary and when it is unnecessary, such as returning to another work. In addition, a caregiver can respond appropriately to a care receiver, and a person in charge can rush to the care receiver. As a result, it is possible to solve the problem that the response is delayed after going to the site once and confirming who is there. However, although a delay of a few seconds occurs in the individual identification, the caregiver can immediately rush in a case of a notification from a place where the caregiver has to immediately rush by giving an entry notification at a time of entry. In addition, when it is sufficient to hear the person specification notification, it is possible to prepare to rush during the individual identification, and thus it is possible to prevent a delay in the response.

The fourth problem can be solved as follows. In the present example embodiment, the caregiver possesses a radio wave output apparatus such as a Bluetooth tag or a smart device, whereby the apparatus can identify the care receiver or the caregiver by the individual identification in the identification processing of the radio wave apparatus. Therefore, even when a caregiver detects a person at a time of use or cleaning, an entry notification is not performed, and the problem that another caregiver performs useless rush is solved.

As described above, the present system can achieve advantageous effects explained in the first example embodiment. In particular, the present system has the following advantageous effects.

The first advantageous effect is that, by installing the information processing apparatus 60 in a space where assistance is required, such as a care facility, a bathroom or a toilet in a residence, entry of a care receiver can be detected and a notification can be given to the caregiver. As a result, it is possible to reduce a burden on a caregiver to watch over a care receiver, and to prevent an accident in a facility.

The second advantageous effect is that the caregiver can perform an operation for assistance in an individual by the user's identification notification in the face authentication processing or the identification processing of the radio wave apparatus after the entry notification, thereby enabling efficient assistance.

The third advantageous effect is that the processing according to the present example embodiment starts by the human detecting sensor 24 detecting a person, and ends when the individual identification is completed and the notification is executed. Therefore, it is not always confirmed by the camera like a watching camera, and it is possible to protect the privacy of the care receiver and to protect the dignity of the care receiver.

The fourth advantageous effect is that the caregiver possesses a Bluetooth tag or a smart device, whereby the caregiver can identify a person by the identification processing of the radio wave apparatus, and even when the person is detected by the human detecting sensor 24, it is detected that the caregiver enters the room, and therefore, the notification cannot be performed. As a result, it is possible to prevent useless notification when the notification is unnecessary, such as when cleaning is performed or when a caregiver uses the room.

The fifth advantageous effect is that, in a case where a plurality of the information processing apparatuses 60 are installed, notification can be set for each installation location, and whether notification is given at the time of entry or after individual identification can be divided, and notification and non-notification settings for each installation location can be set in a notification receiving terminal. As a result, it is possible to prevent useless notification to the caregiver and to prevent useless rush.

Further, the present system has been explained on the assumption that the determination result is included in the notification information consisting of the first notification information and the second notification information, but it is also possible to adopt a configuration in which only the first notification information is first notified and then the notification information consisting of the second notification information and the third notification information is notified. In this case, even in a case where the person who has entered the room is a care recipient, even in a case where the person is a caregiver, the notification is first made to the notification destination at the time of the entry detection. In addition, the present system may adopt a configuration in which only the first notification information is first notified, then the second notification information is notified, and then the third notification information is notified.

Third Example Embodiment

Although a third example embodiment will be mainly explained with reference to FIG. 8 while focusing on differences from the second example embodiment, the various examples explained in the first and second example embodiments can be applied. FIG. 8 is a flowchart for explaining an example of notification processing in an information processing system according to the third example embodiment.

The information processing apparatus according to the present example embodiment differs from the information processing apparatus 60 according to the second example embodiment in the output unit (the output unit 1e in FIG. 1). Therefore, the present example embodiment will also be explained with reference to FIGS. 2 and 3. An output unit in the present example embodiment outputs first notification information, second notification information, and third notification information as one notification information to a notification destination. In short, in the present example embodiment, notification is not performed at a stage when an entry to a room is detected, and notification information is transmitted to a terminal apparatus 50 at a stage when a person who has entered a room is specified.

A flow of such processing will be explained based on FIG. 8. In the processing of FIG. 8, as in the processing of FIGS. 6 and 7, the processing in the information processing apparatus 60 is mainly executed by the CPU 27a, and the processing in the server 40 is mainly executed by the control unit 41.

First, similarly to steps S1 and S2 in FIG. 7, the information processing apparatus 60 monitors whether or not there has been a reaction of a human detecting sensor 24 functioning as an entry sensor (step S11), and determines whether or not an entry of a caregiver has been detected in a stage where there has been a reaction (a stage where YES in step S11) (Step S12). In a case of NO in step S12, in other words, in a case where there is no response from the human detecting sensor 24, the processing waits until the response is performed.

When a care receiver enters a toilet, YES is acquired in step S11, and thereafter, the information processing apparatus 60 determines whether or not the caregiver has entered the toilet (i.e., whether or not the caregiver has been detected) by the equipped radio wave receiving apparatus (step S12). When determining that the person who has entered the toilet is a caregiver (in a case of YES in step S12), the information processing apparatus 60 ends the processing.

On the other hand, in a case where the caregiver is not detected (in a case of NO in step S12) or in a case where the care recipient is detected in a configuration capable of detecting the care recipient, the information processing apparatus 60 performs person authentication processing (individual identification processing) in the same manner as in step S4 in FIG. 7 (step S13). In the person authentication processing, the information processing apparatus 60 transmits image data acquired by a second camera together with an entry detection result (and a determination result) to the server 40 via a network N, and the server 40 performs authentication, based on the image data. As in steps S5 to S7 in FIG. 7, the server 40 determines whether or not the person is registered as a care receiver as a result of the authentication (step S14), performs a person specification notification (step S15) and a person unspecified notification (step S16) according to the determination result, and ends the processing. Note that the person specification notification and the person unspecified notification may include the first notification information indicating that the person has entered the room and the second notification information indicating the determination result, but may be treated as being implicitly included.

With these notifications, according to the present example embodiment, as in the advantageous effect of the second example embodiment, it is possible to solve the problems of watching over and providing assistance to the care receiver, and thus it is possible to reduce a burden on the caregiver and to provide a generous support to the care receiver. However, as described above, in the present example embodiment, the difference from the second example embodiment is that there is no prior notification at the time of entering the room, and the advantageous effect of this point is not achieved.

In the second example embodiment, the third notification information is output after the output of the first notification information and the second notification information, or the second notification information and the third notification information are output after the output of the first notification information. Also in the present example embodiment, any one of the output methods can be selectively set. In short, in the present example embodiment, it is possible to determine whether the notification information is transmitted to the notification destination at a stage when the person who has entered the room is specified, whether the third notification information is transmitted after the transmission of the first notification information and second notification information, or whether the second notification information and third notification information are transmitted after the transmission of the first notification information, with reference to the set information. The set information can be, for example, information set as a notification condition.

This setting can be determined, for example, by the importance of immediacy in operation. In this case, since a delay occurs only by the notification at the time when individual identification is made, the immediacy can be acquired by raising the first report at the time when a person is detected by the human detecting sensor. Next, when the immediacy is required, the first notification information and the second notification information can be set in such a way as to be raised as the first report. In addition, in a case where a plurality of the information processing apparatuses 60 are installed, the caregiver can also set notification or non-notification for each installation location, and thus it is possible to prevent from rushing for unnecessary assistance by reducing unnecessary notification.

Fourth Example Embodiment

In the second and third example embodiments, explanation has been made by giving a toilet as an example of a room, but other types of rooms such as a bathroom may be employed. In the present example embodiment, an example to be used in a bathroom is given with reference to FIG. 9, but various examples explained in the first to third example embodiments can be applied. FIG. 9 is a schematic diagram illustrating a configuration example of an information processing system according to a fourth example embodiment.

As illustrated in FIG. 9, in the information processing apparatus according to the present example embodiment, a part related to excretion information is unnecessary, and the information processing apparatus includes a control box 61 and a person detection/identification box 68 connected to the control box 61 via a cable K2. In FIG. 9, the server 40 and the terminal apparatus 50 are omitted.

The person detection/identification box 68 may be provided inside the bathroom, or may be arranged at a position where entry of a person from a door 71 outside the bathroom can be detected. FIG. 9 illustrates an example in which the person detection/identification box 68 is provided on a back side of a bathtub 70 of the bathroom when facing from the door 71. The control box 61 may also be provided inside the bathroom, or may be provided outside the bathroom.

In the present example embodiment as well, watching of a care receiver can be performed in an information processing apparatus relevant to a so-called edge of a communication network in a care facility or a residence. In the present example embodiment, when the information processing apparatus is installed in a place where entry is desired to be detected in a bathroom, entry can be detected by a human detecting sensor. Further, in this information processing apparatus, person information registered in advance can be used for the person, individual identification can be performed, and the person who has entered the room can be specified based on a result of the individual identification.

In addition, the notification to the terminal apparatus possessed by a caregiver may be executed separately as in the second example embodiment, or may be executed at one time up to information regarding the specified person as in the third example embodiment. In addition, although the bathroom has been explained as an example, a person detection/identification box 68 may be installed, for example, in a room other than a toilet or a bathroom, such as an entry, a bedroom, or a cafeteria of a facility, and may watch over a care recipient.

Other Example Embodiment

[a]

Although the functions of the information processing system and the apparatuses to be included in the system have been explained in the example embodiments, the apparatuses are not limited to the illustrated configuration examples, and it is sufficient that each of the apparatuses can achieve these functions.

[b]

Each of the apparatuses explained in the first to fourth example embodiments may have the following hardware configuration. FIG. 10 is a diagram illustrating an example of a hardware configuration of an apparatus. The same applies to the above-described another example embodiment [a].

An apparatus 100 to be illustrated in FIG. 10 may include a processor 101, a memory 102, and a communication interface (I/F) 103. The processor 101 may be, for example, a microprocessor, a Micro Processor Unit (MPU), a CPU, or the like. The processor 101 may include a plurality of processors. The memory 102 includes, for example, a combination of a volatile memory and a non-volatile memory. The functions of the apparatuses explained in the first to fourth example embodiments are achieved by the processor 101 reading and executing a program stored in the memory 102. At this time, information can be transmitted and received to and from other apparatuses via a communication interface 103 or an input/output interface not to be illustrated.

The program includes an instruction group (or software codes) for causing, when loaded into a computer, a computer to perform one or more of the functions explained in the example embodiments. The program may be stored in a non-transitory computer-readable medium or a tangible storage medium. By way of example, and not limitation, the computer-readable media or tangible storage media include random-access memory (RAM), read-only memory (ROM), flash memory, solid-state drive (SSD) or other memory techniques, CD-ROM, digital versatile disc (DVD), Blu-ray (registered trademark) disk or other optical disk storage, magnetic cassettes, magnetic tape, and magnetic disk storage or other magnetic storage devices. The program may be transmitted on a transitory computer readable medium or a communication medium. By way of example, and not limitation, the transitory computer-readable media or communication media include electrical, optical, acoustic, or other forms of propagated signals.

Note that the present disclosure is not limited to the above-described example embodiments, and can be appropriately modified without departing from the spirit thereof. Further, the present disclosure may be implemented by appropriately combining the example embodiments.

Some or all of the above-described example embodiments may be described as the following supplementary notes, but are not limited thereto.

Supplementary Note 1

An information processing system including:

a sensor configured to detect entry of a person into a room;

a determination unit configured to determine whether a person who enters the room is a care recipient as a user of the room or a caregiver who provides care for the user;

a specification unit configured to specify the person;

a storage unit configured to store an entry detection result by the sensor, a determination result by the determination unit, and a specification result by the specification unit; and an output unit configured to output first notification information indicating the entry detection result, second notification information indicating the determination result, and third notification information indicating the specification result to a notification destination.

Supplementary Note 2

The information processing system according to supplementary note 1, wherein the output unit outputs the second notification information and the third notification information to the notification destination after outputting the first notification information to the notification destination.

Supplementary Note 3

The information processing system according to supplementary note 1, wherein the output unit outputs the third notification information to the notification destination after outputting the first notification information and the second notification information as one notification information to the notification destination.

Supplementary Note 4

The information processing system according to supplementary note 1, wherein the output unit outputs the first notification information, the second notification information, and the third notification information as one piece of notification information to the notification destination.

Supplementary Note 5

The information processing system according to any one of supplementary notes 1 to 4, wherein the storage unit stores, as a notification condition, necessity of notification, and the notification destination, the first notification information, the second notification information, and the third notification information in a case where a notification is required for each care recipient as the user, and the output unit performs output to the notification destination according to the notification condition.

Supplementary Note 6

The information processing system according to supplementary note 5, further including a setting unit configured to set the notification condition.

Supplementary Note 7

The information processing system according to supplementary note 5 or 6, wherein the notification condition includes a condition indicating that, when it is detected that the caregiver who provides care for a care recipient serving as the user enters a room before the care recipient enters the room, no notification is to be performed until the care recipient and the caregiver are no longer in the room subsequently.

Supplementary Note 8

The information processing system according to any one of supplementary notes 5 to 7, wherein the notification condition includes a condition indicating that in a state where a care recipient as the user is in the room, no notification is performed while the caregiver who provides care for the care recipient as the notification destination is in the room.

Supplementary Note 9

An information processing apparatus including:

a sensor configured to detect entry of a person into a room;

a determination unit configured to determine whether a person who enters the room is a care recipient as a user of the room or a caregiver who provides care for the user;

a specification unit configured to specify the person;

a storage unit configured to store an entry detection result by the sensor, a determination result by the determination unit, and a specification result by the specification unit; and an output unit configured to output first notification information indicating the entry detection result, second notification information indicating the determination result, and third notification information indicating the specification result to a notification destination.

Supplementary Note 10

The information processing apparatus according to supplementary note 9, wherein the output unit outputs the second notification information and the third notification information to the notification destination after outputting the first notification information to the notification destination.

Supplementary Note 11

The information processing apparatus according to supplementary note 9, wherein the output unit outputs the third notification information to the notification destination after outputting the first notification information and the second notification information as one piece of notification information to the notification destination.

Supplementary Note 12

The information processing apparatus according to supplementary note 9, wherein the output unit outputs the first notification information, the second notification information, and the third notification information as one piece of notification information to the notification destination.

Supplementary Note 13

An information processing method including:

detecting entry of a person into a room by a sensor;

determining whether a person who enters the room is a care recipient as a user of the room or a caregiver who provides care for the user;

specifying the person;

storing an entry detection result by the sensor, a determination result acquired by determining the person, and a specification result acquired by specifying the person; and outputting first notification information indicating the entry detection result, second notification information indicating the determination result, and third notification information indicating the specification result to a notification destination.

Supplementary Note 14

The information processing method according to supplementary note 13, including outputting the second notification information and the third notification information to the notification destination after outputting the first notification information to the notification destination.

Supplementary Note 15

The information processing method according to supplementary note 13, including outputting the third notification information to the notification destination after outputting the first notification information and the second notification information as one piece of notification information to the notification destination.

Supplementary Note 16

The information processing method according to supplementary note 13, including outputting the first notification information, the second notification information, and the third notification information as one piece of notification information to the notification destination.

Supplementary Note 17

A program for causing a computer to execute information processing of:

detecting entry of a person into a room by a sensor;

determining whether a person who enters the room is a care recipient as a user of the room or a caregiver who provides care for the user;

specifying the person;

storing an entry detection result by the sensor, a determination result acquired by determining the person, and a specification result acquired by specifying the person; and outputting first notification information indicating the entry detection result, second notification information indicating the determination result, and third notification information indicating the specification result to a notification destination.

Supplementary Note 18

The program according to supplementary note 17, wherein the information processing includes outputting the second notification information and the third notification information to the notification destination after outputting the first notification information to the notification destination.

Supplementary Note 19

The program according to supplementary note 18, wherein the information processing includes outputting the third notification information to the notification destination after outputting the first notification information and the second notification information as one piece of notification information to the notification destination.

Supplementary Note 20

The program according to supplementary note 18, wherein the information processing includes outputting the first notification information, the second notification information, and the third notification information as one piece of notification information to the notification destination.

Although the present invention has been explained with reference to the example embodiments, the present invention is not limited to the above. Various modifications that can be understood by a person skilled in the art within the scope of the invention can be made to the configuration and details of the present invention.

This application is based upon and claims the benefit of priority from Japanese Patent Application No. 2021-174624, filed on Oct. 26, 2021, the disclosure of which is incorporated herein in its entirety.

REFERENCE SIGNS LIST

1 INFORMATION PROCESSING SYSTEM
1a SENSOR
1b DETERMINATION UNIT
1c SPECIFICATION UNIT
1d STORAGE UNIT
1e OUTPUT UNIT
10 TOILET BOWL
10a SIDE SURFACE
10b FLAT PORTION
10c EDGE
11 TOILET SEAT
11a TOILET SEAT MAIN BODY
11b TOILET SEAT COVER
24 HUMAN DETECTING SENSOR

25 IMAGE CAPTURE APPARATUS (SECOND CAMERA)
26 INFORMATION COLLECTION UNIT
26*a* RANGE SENSOR
26*b* FIRST CAMERA
27*a* CPU
27*b* CONNECTOR
27*c* USB I/F
27*e* WiFi MODULE
27*f* BLUETOOTH MODULE
40 SERVER
41 CONTROL UNIT
42 STORAGE UNIT
50 TERMINAL APPARATUS
51 DISPLAY SCREEN
52, 53, 54 NOTIFICATION INFORMATION
60 INFORMATION PROCESSING APPARATUS
61 STORAGE HOUSING (CONTROL BOX)
62 BRIDGE PORTION (CROSSOVER)
63 INNER HOUSING (SENSOR BOX)
67 CONTROL UNIT
68 SEPARATE HOUSING (HUMAN DETECTION/IDENTIFICATION BOX)
69 OUTER HOUSING
70 BATHTUB
71 DOOR
100 APPARATUS
101 PROCESSOR
102 MEMORY
103 COMMUNICATION INTERFACE

What is claimed is:

1. An information processing system comprising:
a sensor configured to detect entry of a person into a room;
at least one memory storing instructions; and
at least one processor configured to execute the instructions to do information processing, the information processing includes:
determining whether the person who has entered the room is a care recipient as a user of the room or a caregiver who provides care for the user;
identifying the person who has entered the room;
storing an entry detection result by the sensor, a determination result by the determining, and a specification result by the identifying in the at least one memory; and
outputting first notification information indicating the entry detection result, second notification information indicating the determination result, and third notification information indicating the specification result to a notification destination.

2. The information processing system according to claim 1, wherein the outputting is outputting the second notification information and the third notification information to the notification destination after outputting the first notification information to the notification destination.

3. The information processing system according to claim 1, wherein the outputting is outputting the third notification information to the notification destination after outputting the first notification information and the second notification information as one piece of notification information to the notification destination.

4. The information processing system according to claim 1, wherein the outputting is outputting the first notification information, the second notification information, and the third notification information as one piece of notification information to the notification destination.

5. The information processing system according to claim 1, wherein
the storing includes storing in the at least one memory, as a notification condition, necessity of notification, and the notification destination, the first notification information, the second notification information, and the third notification information in a case where a notification is required, for each care recipient as the user, and
the outputting includes outputting to the notification destination according to the notification condition.

6. The information processing system according to claim 5, wherein the information processing further includes setting the notification condition.

7. The information processing system according to claim 5, wherein the notification condition includes a condition indicating that, when it is detected that the caregiver who provides care for a care recipient serving as the user enters the room before the care recipient enters the room, no notification is performed until the care recipient and the caregiver are no longer in the room subsequently.

8. The information processing system according to claim 5, wherein the notification condition includes a condition indicating that, in a state where a care recipient as the user is in the room, no notification is performed while the caregiver who provides care for the care recipient as the notification destination is in the room.

9. An information processing method comprising:
detecting entry of a person into a room by a sensor;
determining whether the person who has entered the room is a care recipient as a user of the room or a caregiver who provides care for the user;
identifying the person who has entered the room;
storing an entry detection result by the sensor, a determination result acquired by the determining, and a specification result acquired by the identifying; and
outputting first notification information indicating the entry detection result, second notification information indicating the determination result, and third notification information indicating the specification result to a notification destination.

10. The information processing method according to claim 9, wherein the outputting is outputting the second notification information and the third notification information to the notification destination after outputting the first notification information to the notification destination.

11. The information processing method according to claim 9, wherein the outputting is outputting the third notification information to the notification destination after outputting the first notification information and the second notification information as one piece of notification information to the notification destination.

12. The information processing method according to claim 9, wherein the outputting is outputting the first notification information, the second notification information, and the third notification information as one piece of notification information to the notification destination.

13. The information processing method according to claim 9, further comprising storing, as a notification condition, necessity of notification, and the notification destination, the first notification information, the second notification information, and the third notification information in a case where a notification is required, for each care recipient as the user, wherein
the outputting includes outputting to the notification destination according to the notification condition.

14. The information processing method according to claim 9, further comprising setting the notification condition.

15. A non-transitory computer-readable medium storing a program for causing a computer to execute information processing of:

detecting entry of a person into a room by a sensor;

determining whether the person who has entered the room is a care recipient as a user of the room or a caregiver who provides care for the user;

identifying the person who has entered the room;

storing an entry detection result by the sensor, a determination result acquired by the determining, and a specification result acquired by the identifying; and outputting first notification information indicating the entry detection result, second notification information indicating the determination result, and third notification information indicating the specification result to a notification destination.

16. The non-transitory computer-readable medium according to claim 15, wherein outputting is outputting the second notification information and the third notification information to the notification destination after outputting the first notification information to the notification destination.

17. The non-transitory computer-readable medium according to claim 15, wherein the outputting is outputting the third notification information to the notification destination after outputting the first notification information and the second notification information as one piece of notification information to the notification destination.

18. The non-transitory computer-readable medium according to claim 15, wherein the outputting is outputting the first notification information, the second notification information, and the third notification information as one piece of notification information to the notification destination.

19. The non-transitory computer-readable medium according to claim 15, wherein the information processing includes storing, as a notification condition, necessity of notification, and the notification destination, the first notification information, the second notification information, and the third notification information in a case where a notification is required, for each care recipient as the user, and the outputting includes outputting to the notification destination according to the notification condition.

20. The non-transitory computer-readable medium according to claim 15, wherein the information processing includes setting the notification condition.

\* \* \* \* \*